United States Patent
Anderson et al.

(10) Patent No.: US 9,295,426 B2
(45) Date of Patent: Mar. 29, 2016

(54) DETECTION OF A PHYSIOLOGIC PARAMETER WITH A PROBE

(75) Inventors: Edward J. Anderson, Hopkins, MN (US); Brandon W. Reynolds, Prior Lake, MN (US); Kent R. Winger, Prior Lake, MN (US); Victor E. Kimball, Burnsville, MN (US)

(73) Assignee: ExoStat Medical, Inc., Prior Lake, MN (US)

( * ) Notice: Subject to any disclaimer, the term of this patent is extended or adjusted under 35 U.S.C. 154(b) by 1432 days.

(21) Appl. No.: 13/036,832

(22) Filed: Feb. 28, 2011

(65) Prior Publication Data

US 2011/0152646 A1    Jun. 23, 2011

Related U.S. Application Data

(63) Continuation of application No. 11/185,058, filed on Jul. 20, 2005, now abandoned, which is a continuation-in-part of application No. 10/366,903, filed on Feb. 14, 2003, now Pat. No. 8,996,090, which is a continuation-in-part of application No. 10/162,028, filed on Jun. 3, 2002, now abandoned.

(51) Int. Cl.
*A61B 5/05* (2006.01)
*A61B 5/00* (2006.01)
(Continued)

(52) U.S. Cl.
CPC . *A61B 5/682* (2013.01); *A61B 5/01* (2013.01); *A61B 5/1459* (2013.01);
(Continued)

(58) Field of Classification Search
CPC ........ A61B 5/682; A61B 5/6885; A61B 5/01; A61B 5/14539; A61B 5/42; A61B 5/412; A61B 5/1459; A61B 5/14546; A61B 2562/02; A61B 8/12; A61B 5/1473; A61B 8/06; A61B 2562/247; A61B 5/14532
See application file for complete search history.

(56) References Cited

U.S. PATENT DOCUMENTS

| 3,334,623 | A | * | 8/1967 | Hillier | ............... A61B 5/14542 204/403.06 |
| 3,380,929 | A | | 4/1968 | Petersen | |

(Continued)

FOREIGN PATENT DOCUMENTS

| EP | 0241294 A2 | 10/1987 |
| EP | 1080684 A2 | 3/2001 |

(Continued)

OTHER PUBLICATIONS

Vurek et al., "A Fiber Optic PCO2 Sensor," Annals of Biomedical Engineering, 2, 449-510 (1983).

(Continued)

*Primary Examiner* — Michael Kahelin
*Assistant Examiner* — Tho Tran
(74) *Attorney, Agent, or Firm* — Barbara A. Wrigley; Fox Rothschild LLP

(57) ABSTRACT

The invention provides a device for contacting a surface of a patient's body to determine a physiologic parameter in a measurement region of a tissue of the patient. The device typically comprises a sensor responsive to the physiologic parameter and a probe housing the sensor. The probe is constructed to allow the sensor to be secured at a sensing site adjacent to the measurement region, without disturbing the blood flow within the measurement region of the tissue. The device may also include a means for reducing interference in the sensing area. Preferably, the device further comprises an indicating means operably connected to the sensor for indicating an analyte quantity and/or concentration associated with the physiologic parameter.

43 Claims, 10 Drawing Sheets

(51) Int. Cl.
*A61B 5/01* (2006.01)
*A61B 5/1459* (2006.01)
*A61B 5/145* (2006.01)
*A61B 5/1473* (2006.01)
*A61B 8/06* (2006.01)
*A61B 8/12* (2006.01)

(52) U.S. Cl.
CPC ........ *A61B 5/14539* (2013.01); *A61B 5/14546* (2013.01); *A61B 5/412* (2013.01); *A61B 5/42* (2013.01); *A61B 5/6885* (2013.01); *A61B 5/1473* (2013.01); *A61B 5/14532* (2013.01); *A61B 8/06* (2013.01); *A61B 8/12* (2013.01); *A61B 2562/02* (2013.01); *A61B 2562/247* (2013.01)

(56) References Cited

U.S. PATENT DOCUMENTS

| | | | |
|---|---|---|---|
| 3,681,255 | A | 8/1972 | Wilfore et al. |
| 3,888,237 | A * | 6/1975 | Mori ............... A61B 1/00098 204/403.06 |
| 3,892,058 | A | 7/1975 | Komatsu et al. |
| 3,905,889 | A | 9/1975 | Macur et al. |
| 3,946,724 | A | 3/1976 | La Balme |
| 4,016,863 | A | 4/1977 | Brantigan |
| 4,116,336 | A | 9/1978 | Sorensen et al. |
| 4,274,423 | A * | 6/1981 | Mizuno ............ A61B 5/0215 600/488 |
| 4,423,736 | A * | 1/1984 | DeWitt ............ A61B 5/0059 600/306 |
| 4,474,183 | A | 10/1984 | Yano et al. |
| 4,632,119 | A | 12/1986 | Reichstein |
| 4,637,403 | A * | 1/1987 | Garcia ............ A61B 5/1411 600/368 |
| 4,643,192 | A | 2/1987 | Fiddian-Green |
| 4,703,756 | A * | 11/1987 | Gough et al. ............ 600/347 |
| 4,722,348 | A | 2/1988 | Ligtenberg et al. |
| 4,771,782 | A | 9/1988 | Millar |
| 4,830,013 | A | 5/1989 | Maxwell |
| 4,850,358 | A | 7/1989 | Millar |
| 4,901,735 | A | 2/1990 | Von Berg |
| 4,953,553 | A | 9/1990 | Tremulis |
| 4,966,148 | A | 10/1990 | Millar |
| 4,979,948 | A * | 12/1990 | Geddes et al. ............ 606/33 |
| 4,981,470 | A | 1/1991 | Bombeck, IV |
| 5,000,180 | A | 3/1991 | Kuypers et al. |
| 5,046,497 | A | 9/1991 | Millar |
| 5,085,223 | A | 2/1992 | Lars et al. |
| 5,105,812 | A | 4/1992 | Corman |
| 5,109,849 | A | 5/1992 | Goodman et al. |
| 5,111,817 | A | 5/1992 | Clark et al. |
| 5,117,827 | A | 6/1992 | Stuebe et al. |
| 5,165,407 | A | 11/1992 | Wilson et al. |
| 5,166,990 | A | 11/1992 | Riccitelli et al. |
| 5,174,290 | A | 12/1992 | Fiddian-Green |
| 5,271,405 | A | 12/1993 | Boyer et al. |
| 5,280,786 | A | 1/1994 | Wlodarczyk et al. |
| 5,341,803 | A | 8/1994 | Goldberg et al. |
| 5,372,136 | A | 12/1994 | Steuer et al. |
| 5,411,022 | A | 5/1995 | McCue et al. |
| 5,423,320 | A | 6/1995 | Salzman et al. |
| 5,425,371 | A | 6/1995 | Mischenko |
| 5,456,251 | A | 10/1995 | Fiddian-Green |
| 5,480,611 | A | 1/1996 | Mills et al. |
| 5,579,763 | A | 12/1996 | Weil et al. |
| 5,672,515 | A | 9/1997 | Furlong |
| 5,690,215 | A | 11/1997 | Kimball et al. |
| 5,697,366 | A | 12/1997 | Kimball et al. |
| 5,710,371 | A | 1/1998 | Czernecki et al. |
| 5,714,121 | A | 2/1998 | Alderete et al. |
| 5,771,891 | A | 6/1998 | Gozani |
| 5,788,631 | A | 8/1998 | Fiddian-Green |
| 5,800,420 | A * | 9/1998 | Gross ............... A61K 9/0021 204/280 |
| 5,902,248 | A | 5/1999 | Millar et al. |
| 5,916,155 | A | 6/1999 | Levinson et al. |
| 5,976,085 | A | 11/1999 | Kimball et al. |
| 6,055,447 | A | 4/2000 | Weil et al. |
| 6,071,237 | A | 6/2000 | Weil et al. |
| 6,125,290 | A | 9/2000 | Miesel |
| 6,125,291 | A | 9/2000 | Miesel |
| 6,143,150 | A | 11/2000 | Nagai et al. |
| 6,144,866 | A | 11/2000 | Miesel |
| 6,198,952 | B1 | 3/2001 | Miesel |
| 6,216,024 | B1 | 4/2001 | Weil et al. |
| 6,258,046 | B1 | 7/2001 | Kimball et al. |
| 6,264,612 | B1 * | 7/2001 | McConnell et al. ......... 600/486 |
| 6,411,834 | B1 | 6/2002 | Nagai |
| 6,915,147 | B2 | 7/2005 | Lebel et al. |
| 2002/0001335 | A1 * | 1/2002 | Lee ............... 374/208 |
| 2002/0028990 | A1 | 3/2002 | Shepherd et al. |
| 2002/0072657 | A1 * | 6/2002 | Bousquet et al. ............. 600/310 |
| 2005/0043626 | A1 | 2/2005 | Marciante et al. |

FOREIGN PATENT DOCUMENTS

| | | |
|---|---|---|
| WO | WO 94/23645 A | 10/1994 |
| WO | WO 98/06323 A | 2/1998 |
| WO | WO 99/16346 A | 4/1999 |
| WO | WO 01-28416 | 4/2001 |

OTHER PUBLICATIONS

International Search Report, U.S. Appl. No. PCT/US2003/016033, Dec. 1, 2003, 2 pgs.

Supplemental Partial European Search Report of Oct. 19, 2006 for Applic No. EP 03 75 6193.

* cited by examiner

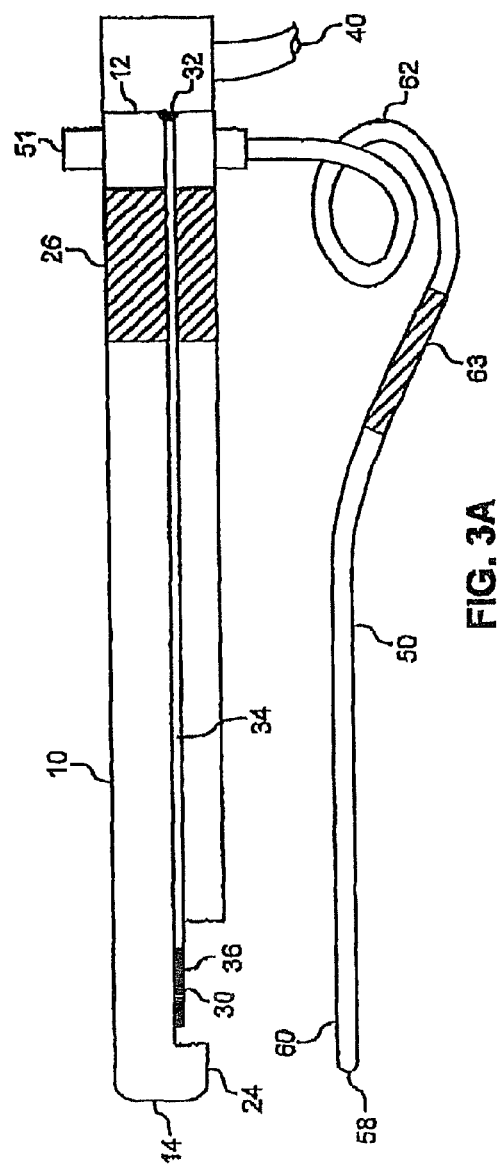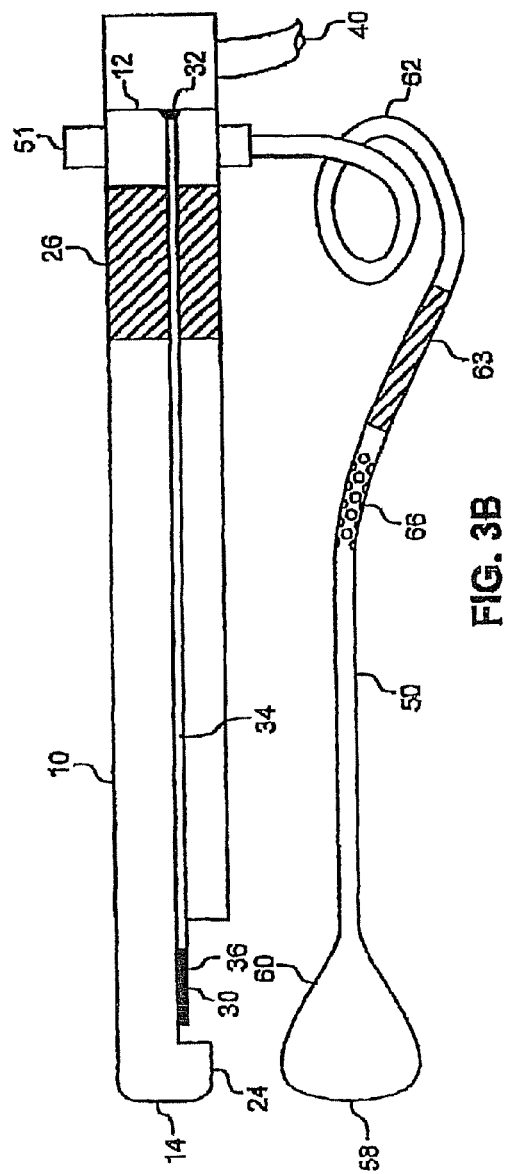

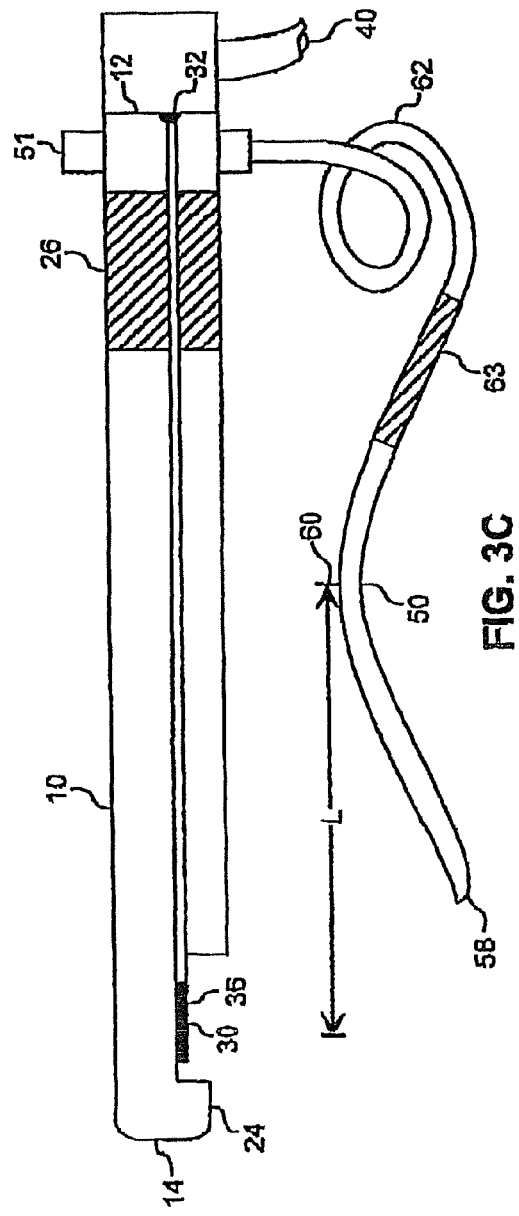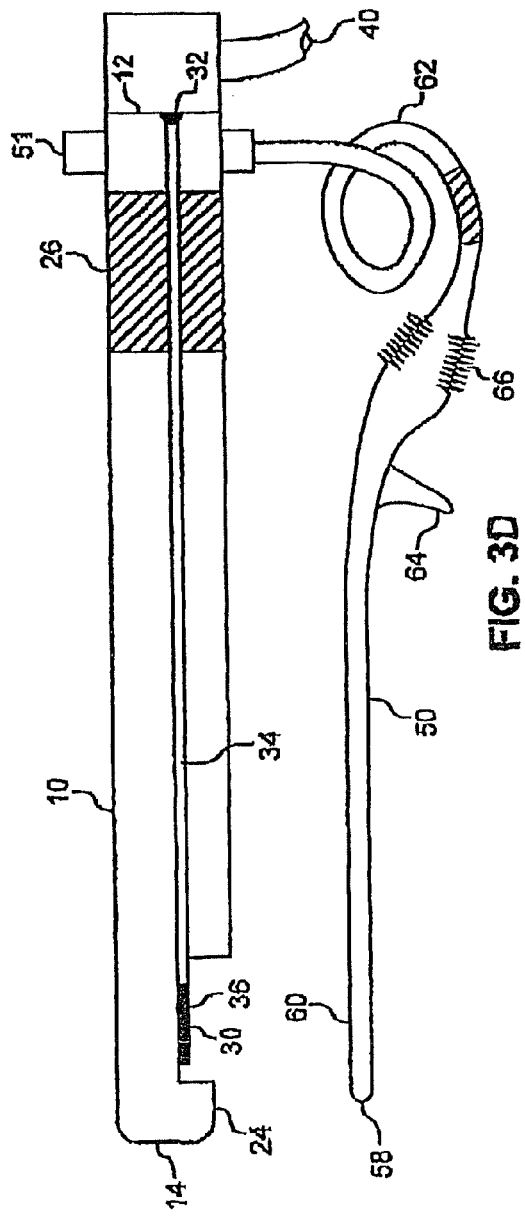

DETECTION OF A PHYSIOLOGIC PARAMETER WITH A PROBE

CROSS REFERENCE TO RELATED APPLICATIONS

This application is a continuation of U.S. application Ser. No. 11/185,058, filed Jul. 20, 2005; which is a continuation-in-part of U.S. application Ser. No. 10/366,903, filed Feb. 14, 2003, now abandoned; which is a continuation-in-part of U.S. application Ser. No. 10/162,028, filed Jun. 3, 2002, now abandoned, the entireties of which are hereby incorporated by reference.

TECHNICAL FIELD

The present invention relates generally to devices and methods for noninvasive detection of a physiologic parameter within a tissue of a patient. More particularly, the invention relates to such devices and methods that allow a probe containing at least one sensor to be placed adjacent to a surface of the tissue, without substantially disturbing blood flow in the tissue, and/or without interference from interfering fluids or radiation.

BACKGROUND

There is a continuing need for improved devices and methods for determining one or more physiologic parameters of a patient. Often, such physiologic parameters are determined by detecting or measuring the quantity of concentration of an analyte associated with the physiologic parameter within a tissue of a patient. Noninvasive techniques for analyte detection are preferred over invasive detection techniques because invasive procedures result in stress and discomfort to patients. For example, conventional detection of blood analytes often involves drawing a sample of blood from the patient and subjecting the sample to in vitro testing for a specific analyte. This technique suffers from a number of drawbacks. First, drawing blood requires the puncturing of a patient's skin and creates a risk of infection. Second, hypodermic needles used in drawing blood may also pose a risk of accidental infection to health care professionals such as phlebotomists who routinely use the needles and sanitary workers who handle contaminated needles. Third, the technique of drawing blood and in vitro testing is not easily adaptable for real-time and continuous monitoring of changes in analyte.

Nevertheless, analyte detection is of course an essential process in medical diagnosis. For example, it is necessary to determine the concentration of glucose in blood in diabetic patients on a regular basis. U.S. Pat. No. 5,771,891 to Gonzani describes a non-invasive blood analyte concentration monitoring apparatus for analyzing blood analytes such as glucose. This patent describes an apparatus that operates by stimulating an endogenous tissue with an electrical or magnetic stimulus, detecting a response of the tissue to the stimulus, correlating the response to a quantitative measure of the analyte concentration, and indicating the quantitative measure. It may also be desirable to measure the hematocrit concentration to determine the oxygen carrying capacity of a patient's blood. U.S. Pat. No. 5,372,136 to Steuer et al. describes a method for determining the concentration of a blood analyte such as hematocrit by passing at least two, preferably three, predetermined wavelengths of light onto or through body tissues such as the finger, earlobe or scalp and using mathematical manipulation of the detected values to compensate for spectral interference resulting from the presence of numerous species in body tissue.

There is also widespread interest in blood gas concentration for a number of reasons. For example, a patient may be rendered unconscious during surgery through administration of gaseous anesthesia such as nitrous oxide, desflurane, enflurane, halothane, isoflurane, methoxyflurane or sevoflurane. These gases are administered by allowing the patient to inhale the gases into his or her lungs. Once the gas is in the circulatory system, it passes through the blood-brain barrier into the brain where the gas increases the neurocellular threshold for firing. The partial pressure of gas in the blood provides an indication of the pharmacodynamics of the gas with respect to the brain such as change in neurological metabolic rate. Thus, analyzing blood with respect to anesthesia content is useful to ensure that the patient is neither overly sedated nor insufficiently anesthetized. Excessive sedation may cause permanent injury to the patient, sometimes resulting in death, and insufficient sedation is ineffective to suppress pain.

As another example, very low blood flow, or low "systemic perfusion," occurs typically because of low aortic pressure and can be caused by a number of factors, including hemorrhage, sepsis, and cardiac arrest. The body responds to such stress by reducing blood flow to the gastrointestinal tract to spare blood for other, more critical organs. Thus, when blood flow from the heart is reduced, blood flow is generally maintained to critical organs, such as the brain, which will not survive long without a continuous supply of blood, while blood flow is restricted to less critical organs, whose survival is not as threatened by a temporary reduction in blood flow. For example, blood flow to the stomach, intestines, esophagus and oral/nasal cavity is drastically reduced when there is a reduced blood flow from the heart or when a patient is experiencing circular shock. For this reason, decreased blood flow to the splancnic blood vessels provides an indication of perfusion failure in a patient. Physicians commonly take advantage of this phenomenon by taking $CO_2$ and pH measurements in the stomach and intestine to assess perfusion failure.

Assessment of $CO_2$ concentration in the less critical organs, i.e., those organs to which blood flow is reduced during perfusion failure, has also been useful in perfusion assessment. Carbon dioxide production, which is associated with metabolism, continues in tissues even during conditions of low blood flow. The concentration of $CO_2$ builds up in tissues experiencing low blood flow because $CO_2$ is not rapidly carried away. Correspondingly, $O_2$ is consumed as $CO_2$ is generated. This $CO_2$ build-up (an increase in partial pressure of $CO_2$ ($pCO_2$)) in the less critical organs in turn results in a decrease in pH. Therefore, perfusion failure is commonly assessed by measuring pH or $pCO_2$ at these sites, especially in the stomach and intestines. For examples of catheters used to assess pH or $pCO_2$ in the stomach or intestines, see, e.g., U.S. Pat. Nos. 3,905,889; 4,016,863; 4,632,119; 4,643,192; 4,981,470; 5,105,812; 5,117,827; 5,174,290; 5,341,803; 5,411,022; 5,423,320; 5,456,251; and 5,788,631.

A number other patents discuss the measurement tissue analytes. U.S. Pat. No. 5,579,763 to Weil et al., for example, discusses a minimally invasive method for detecting a chemical characteristic in the gastrointestinal system of a patient who is in critical condition. In this patent, the specification focuses on taking measurements of carbon dioxide in a patient's esophagus using a catheter having a carbon dioxide sensor at its tip. Similarly, U.S. Pat. No. 6,055,447 to Weil also relate to carbon dioxide measurements and describes that the sensor may be placed against mucosal surface in the mouth or nose other than the sublingual area. In addition, U.S. Pat. No. 6,216,024 to Weil et al. discusses a device for assessing perfusion failure that comprises a carbon dioxide sensor for lying against a mucosal surface of the upper digestive/respiratory tract of a patient, an isolating means for inhibiting air flow around the mucosal surface, and indicating means operatively connected to the sensor for indicating a degree of perfusion failure of the patient.

Similarly, it is important to be able to accurately determine the amount of oxygen in the bloodstream or the amount of oxygen in the surrounding tissue. For example, $PO_2$ in blood may be analyzed by using an oxygen electrode based on the so-called Clark's electrode system, described in U.S. Pat. No. 5,710,371 to Czernecki et al. Such electrode systems are based on electrochemical reduction of $O_2$ at an anode made from an element such as tungsten or molybdenum. This type of analyte-sensitive portion requires the diffusion of $O_2$ from blood across a membrane to a liquid electrolyte in which $O_2$ is reduced at the anode/electrolyte interface, thereby generating an electrical current that corresponds to the $PO_2$ in the blood sample. However, improper maintenance may subject the liquid electrolyte to evaporation or drying, thereby compromising the accuracy of analyte detection. Thus, this approach suffers from the drawback that the electrode apparatus must be meticulously maintained.

U.S. Pat. No. 5,423,320 to Salzman et al. describes a method for measuring or monitoring intraluminal gastrointestinal $pCO_2$ and $pO_2$. The method involves providing a catheter having a gas sensor, a $CO_2$ and/or an $O_2$ sensor, at a distal tip that is placed within a patient. The sensor is coupled to an output signal generator and/or recorder external to the patient. The catheter may, for example, be a nasojejunal orjejunostomy catheter, wherein the tip of the catheter is placed adjacent to patient tissue, e.g., stomach, colon, rectum, or jejunum tissue, to detect for tissue analyte in situ. Improper placement of such a sensor through use of the catheter may cause blanching of the tissue in which analyte is measured, i.e., occlusion of fluid flow therein, Moreover, during use, this type of device is highly susceptible to being inadvertently rotated to an improper angle or otherwise moved out of proper position for accurate analyte detection.

Thus, there is a need for a device to detect regional (local) or global (systemic) tissue perfusion in a number of contexts. Such devices may be used, for example, as a continuous monitor for extended time periods associated with surgical procedures and with recovery in an intensive care unit that involves a lengthy stay. Alternatively, a single-use version of such a device may be more appropriate for triage use in an emergency room or nursing home. In each of these applications, different $CO_2$ and/or $O_2$ sensing means and different product configurations may be more appropriate depending on the applications requirements for ease-of-use, cost, and response time. For example, either a single use sensor/probe that is discarded after every use or a reusable sensor/probe with or without a disposable sheath to minimize cross-contamination between patients may be utilized. In either case, an indicating means may be provided that is integral to the devices or linked to the device via an electronic, optical, or electromagnetic radiation means. However, since therapeutic decisions may be made based on the sensor readings, the sensor must accurately respond to analytes within tissue and not be compromised by ambient air or other contaminants.

There are a number of challenges associated with the accuracy of non-invasive detection of $CO_2$ and/or $O_2$ in exposed tissue. Referring to $CO_2$ detection as an example, a patient's tissue and surrounding ambient air often exhibit large differences in their respective concentrations of $CO_2$ and $O_2$. If a tissue with a high concentration of $CO_2$ is exposed to ambient air with a low concentration of $CO_2$, a measured $CO_2$ value at the surface of the tissue will have a concentration between the high and the low. This difference can be small or large depending on the how analyte from the deeper tissue diffuses to the surface tissue, how the analyte diffuses from the surrounding environment into the tissue, the physical properties of the tissue, and whether normal blood flow is maintained in the tissue.

It has now been discovered that various factors may compromise the usefulness or accuracy of measurement for certain tissue analytes associated with useful physiologic parameters, in particular, gaseous analytes such as $O_2$ and $CO_2$. For example, as noted above, tissue blanching tends to decrease the concentration of $O_2$ in the blanched area, and a sensor may also be moved out of proper position during measurement. Thus, there is a need in the art for a device for accurate, useful yet noninvasive detection of an analyte, particularly a gaseous analyte, within a tissue of a patient. Such a device would be useful, e.g., to measure perfusion failure or to monitor the concentration of anesthesia during surgery.

SUMMARY OF THE INVENTION

Accordingly, it is an object of the present invention to overcome the above-mentioned disadvantages of the prior art by providing a device that provides for non-invasive and accurate determination of a physiologic parameter of a patient within a tissue of a patient.

It is another object of the invention to provide a device that can be used to measure physiologic parameters locally/regionally and/or globally/systemically.

It is another object of the invention to provide a device that can be used to measure physiologic parameters including respiratory, mechanical and metabolic.

It is another object of the invention to provide a device that can be used to measure physiologic parameters such as $O_2$ saturation levels.

It is another object of the invention to provide a device that can be used to measure physiologic parameters such as pulse, blood flow, blood pressure and other parameters associated with a beating heart.

It is another object of the invention to provide a device that can be used to measure physiologic parameters such as tissue analytes including carbon dioxide, oxygen, and anesthetic gases. It is a further object of the invention to provide a method to measure other physiologic parameters through the use of such a device such as glucose, pyruvate, acetyl-CoA, citrate, isocitrate, alpha-ketoglutarate, succinyl-CoA, ADP, ATP, succinate, fumarate, malate oxaloacetate, NAD, NADH, and all other analytes associated with the tricarboxylic acid cycle.

Additional objects, advantages and novel features of the invention will be set forth in part in the description which follows, and in part will become apparent to those skilled in the art upon examination of the following, or may be learned by routine experimentation during the practice of the invention.

In a general aspect, then, the present invention relates a device for contacting a surface of a tissue within a patient's body to determine a physiologic parameter of the patient. The device provides a sensor responsive to the physiologic parameter and a means for preventing application of excessive pressure to the tissue at a measurement region in the tissue. The sensor is located within a sensing area adjacent to the measurement region. The means for preventing application of excessive pressure allows for substantially undisturbed blood flow in the tissue when contact is established between the device and the tissue. Typically, the physiologic parameter may be associated with parameters such as $O_2$, blood flow, blood pressure, heart beat or pulse and/or tissue analytes. The device may be constructed to engage in trans-tissue or intra-tissue measurement of the quantity or concentration of the analyte. The tissue may be epithelium; connective; muscle or nerve. The mucosa is a tissue that is well suited for measurements utilizing the device of the present invention. In an alternative embodiment, the device of the present invention may also be used on the epidermis and trans-tissue measurements are taken as noted above. An indicating means may also be provided and is operably connected to the sensor for indicating analyte concentration in the patient.

The inventive device may also include a means for reducing interference in an area adjacent to the measurement region. In some instances, the means for reducing interference is adapted to reduce interference from electromagnetic radiation. In other instances, the means for reducing interference may be adapted to reduce interference from a gaseous or liquid fluid. In one embodiment of the present invention the interference reducing means comprises an isolating means for preventing analyte from dissipating from the sensing area and for allowing analyte to come into equilibrium within the sensing area. The isolating means may represent an integral portion of a probe or be sized to fit into the nares, mouth, or cheek of the patient or adapted for placement on the epidermis.

The means for preventing application of excessive pressure may form a portion of the device that is composed of a material that allows the portion to deform in response to force applied to the device so as to avoid substantial blanching the tissue. The material may be elastically and optionally plastically deformable such as a polymer selected from the group consisting of polyethylene, polypropylene, polybutylene, polyamide, polyimide, polyester, perfluorinated polymer, polystyrene, poly (vinyl chloride) and elastomers. In some instances, the means for preventing application of excessive pressure may be provided in the form of a holding means for securing the device immovably adjacent to the surface of the tissue. For example, the holding means may include a clip or a handle. The holding means may be adapted to secure the device adjacent to the tissue without applying pressure greater than about $1.5 \times 10^4$ pascals to the tissue.

The device may include one or more sensors. The invention is particularly suited for the measurement of physiologic parameters including mechanical, respiratory and metabolic parameters. There exists an advantage to the physician in taking at least one measurement from each of these three categories of physiologic parameters because the combination of these measurements provides a more complete data set to the physician allowing her to more accurately diagnosis the medical condition. Thus, the invention is particularly suited for use with a sensor responsive to parameters such as a gas, e.g., oxygen, carbon dioxide, nitrous oxide, desflurane, enflurane, halothane, isoflurane, methoxyflurane, and sevoflurane. In addition, the invention is also particularly suited for use with a sensor responsive to other parameters such as tissue pH, blood pressure, blood flow, pulse, heart contraction and tissue analytes. In particular the sensor may measure physiologic parameters either directly through such means as laser-doppler, ultrasound, microspheres, radioactive isotopes and other such means, or indirectly through the measurement of tissue pH, temperature, $CO_2$, $pCO_2$, $O_2$, glucose, pyruvate, acetyl-CoA, citrate, isocitrate, alpha-ketoglutarate, succinyl-CoA, ADP, ATP, succinate, fumarate, malate oxaloacetate, NAD, NADH, and other analytes associated with the tricarboxylic acid cycle. To assure the accuracy and/or precision of the performance of device, the device may include a temperature detecting means for detecting temperature at the sensor. In some instances, the temperature detecting means is detachable with respect to the device.

The device may further include a sheath covering the device. The sheath may be reusable or disposable. Such a sheath may be employed irrespective of whether the device is adapted for single use or multiple uses. The sheath typically has a selectively permeable portion that allows transmission of an analyte therethrough. For example, the selectively permeable portion may be formed from a permeable silicone or other porous membrane. For ease in handling, the sheath may include a rigid portion.

The sensor may be of any type suitable to effect determination of a physiologic parameter with some degree of accuracy. For example, the sensor may be responsive to analyte concentration through a chemical reaction with a reactant. In some instances, the sensor is constructed to be responsive to analyte concentration through absorption, emission or modification of electromagnetic radiation within the tissue. In addition or in the alternative, the sensor may be constructed to be responsive to analyte concentration through absorption, emission or modification of electromagnetic radiation in the sensing area. In either case, the radiation may be ultraviolet, visible, near infrared, or far infrared. Optimally, a Severinghaus-type sensor may be used. Furthermore, the sensor may be responsive to analyte concentration through generation or alteration of an electrical current.

In another embodiment, the invention provides a device that includes a sensor and a means for reducing interference in a sensing area adjacent to a measurement region in the tissue. As before, the sensor is responsive to the physiologic parameter and located within the sensing area and within the probe. In such an embodiment, the interference reducing means represents an integral portion of a probe.

In a further embodiment, the device includes a sensor responsive to the physiologic parameter and a probe containing the sensor. The probe is constructed to allow it to be secured to a sensing site adjacent to a measurement region in the tissue with or without an adhesive and without substantially disturbing blood flow within the tissue site of measurement. For example, if the device is placed on mucosal tissue the use of an adhesive or gel may or may not be desirable. If the device is place on the epidermis the use of an adhesive or gel may lend additional support to securing the device to the sensing site. If adhesives and/or gels are used they releasably secure the contact area of the device to the surface of the sensing site, e.g. mucosal, epidermal, etc. Optionally, the sensor is detachable with respect to the probe. Sensors that are used to measure tissue analytes may contain a chemical that changes color in the presence of an analyte associated with the physiologic parameter.

In still another embodiment, the invention relates to a method for determining a physiologic parameter of a patient. A sensor is provided that is responsive to the physiologic parameter of a patient. Physiologic parameters may include but are not limited to analytes, blood flow, tissue pH, and tissue temperature. Examples of analytes include gases, $CO_2$, $pCO_2$, $O_2$, glucose, pyruvate, acetyl-CoA, citrate, isocitrate, alpha-ketoglutarate, succinyl-CoA, ADP, ATP, succinate, fumarate, malate oxaloacetate, NAD, NADH, and other analytes associated with the tri-carboxylic acid cycle. The probe is placed on a sensing site adjacent to a measurement region of the patient's body tissue without substantially disturbing blood flow within the tissue being measured. The sensor contained within the probe then detects the physiologic parameter being measured.

In some instances, the sensor is exposed to an analyte associated with the physiologic parameter at a predetermined concentration in at least one calibrant. This may be carried out before and/or after detection of the sensor response to the physiologic parameter.

In addition, the device may optionally be placed in contact with the measurement site in a manner so as to completely or substantially enclose the sensor within the sensing area of the device. Typically, the concentration of an analyte associated with a physiologic parameter in the sensing area of the device and/or the sensing or measurement site may be allowed to reach an equilibrium level. Often, this involves substantially immobilizing the device with respect to the surface of the sensing site for a predetermined period of time. During this period, the detecting step may be initiated, repeated, or performed continuously.

Optionally, the method may further involve correlating the response of the sensor to a condition of the patient. The condition may be a regional or systemic condition. In particular, the invention is particularly suited for deter mining perfusion failure, tissue gas concentration, tissue pH and tissue activity. The correlation may be carried out using a predictive algorithm, endpoint detection and/or verification, and/or univariate, multivariate, or neural network analysis.

In a yet further embodiment, the invention relates to a method for determining a physiologic parameter of a patient. As before, the method provides a sensor responsive to the physiologic parameter of the patient. The probe containing the sensor is placed on a sensing site adjacent to the measurement region of the tissue. The sensing site may be the epidermis while the tissue being measured is muscle, blood, or some other tissue below the epidermis. The method further involves detecting the response of the sensor to the physiologic parameter while preventing interfering fluid ingress into the sensing area of the device.

BRIEF DESCRIPTION OF DRAWINGS

The invention is described in detail below with reference to the following figures:

FIG. 1A illustrates the device in cross-sectional view showing an elongated probe comprising an integrated isolating means that includes a portion that forms a cowl, a sensor located in a sensing area defined in part by the cowl, an optional holding means for securing the probe to a surface of a patient, and a flexible portion adapted to elastically deform in response to a force. FIG. 1B illustrates a portion of the device around the isolating means.

FIG. 2A illustrates a probe and sensor configuration with a grip. FIG. 2B illustrates the probe and sensor configuration of FIG. 2A with a selectively permeable membrane. FIG. 2C illustrates a device configuration that includes a plurality of fiber optic fibers. FIG. 2D illustrates a device configuration with low dead space. FIG. 2E illustrates a device configuration that allows for intra-tissue measurement.

FIGS. 3A-3D, collectively referred to as FIG. 3, illustrate various optional clips in combination with the probe and sensor configuration illustrated in FIG. 2A.

FIG. 6A illustrates in cross-sectional view a device that employs a sensor comprising an analyte-sensitive portion on a substrate. FIG. 6B illustrates the sensor of the device illustrated in FIG. 6A. FIG. 6C illustrates in cross-sectional view a device that employs a sensor comprising a plurality of analyte-sensitive portions on a substrate. FIG. 6D illustrates the sensor of the device illustrated in FIG. 6C.

FIGS. 7A and 7B illustrate a three-piece and a single-piece version of the disposable sheath, respectively.

DETAILED DESCRIPTION OF THE INVENTION

Definitions and Nomenclature

Figure 1A:
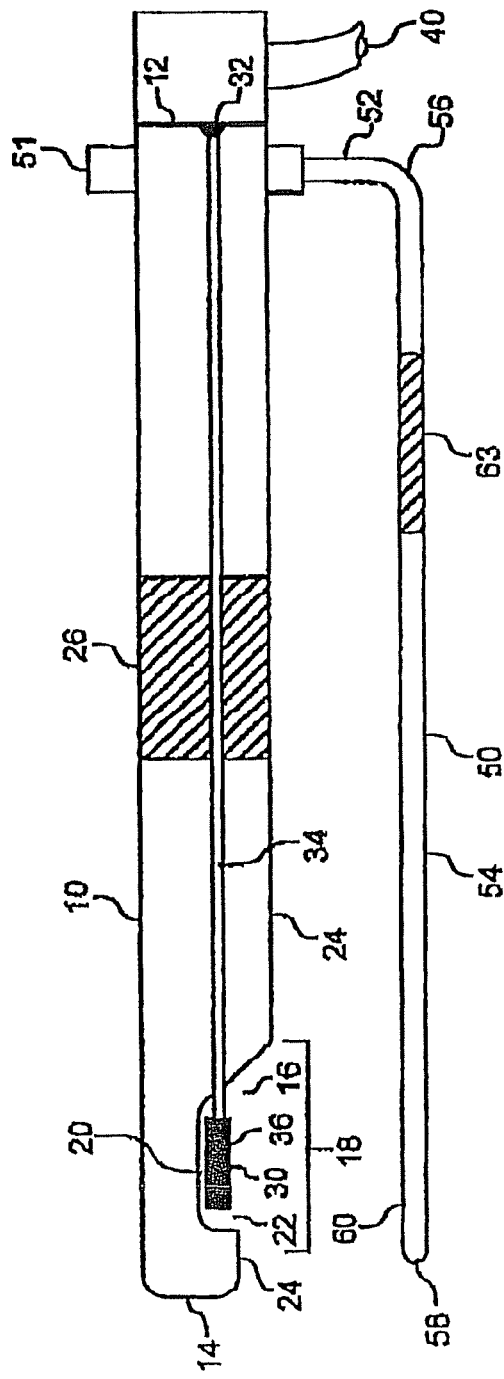
FIGS. 1A-1B, collectively referred to as FIG. 1, illustrate a device of the present invention.

Before the inventive devices and methods are disclosed and described, it is to be understood that this invention is not limited to sensor designs, measurement techniques, or the like, as such may vary. It is also to be understood that the terminology used herein is for the purpose of describing particular embodiments only and is not intended to be limiting.

It must be noted that, as used in the specification and the appended claims, the singular forms "a," "an," and "the" include plural referents unless the context clearly dictates otherwise. The term "adjacent" as used herein (e.g., "adjacent to the surface") means near or against, e.g., at a distance from the mucosal surface that allows acceptably accurate measurement of the analyte. In general, it is preferable that the probe is contacted with the surface of the tissue containing the analyte.

The term "blanch" or "blanching" as used herein refers to a condition wherein sufficient pressure is applied to a tissue to cause occlusion of fluid flow, typically blood flow, within the tissue. For example, use of a tourniquet may cause blanching of tissue contacted by the tourniquet.

The term "calibrant" as used herein refers to a substance, typically liquid, that contains an analyte or an analyte equivalent in a predetermined proportion. The calibrant is used as a reference in calibrating an instrument for detecting the analyte in a sample.

The term "analyte" is used herein in its ordinary sense and refers to a substance with a distinct molecular composition that is being measured by an analytical procedure using the inventive device.

The term "elastically deformable" as used herein refers to a material property that allows the shape of the material to be altered in response to an applied force and that returns the material to its initial shape when the applied force is removed.

Typically, deformation is inversely proportional to the elastic modulus of the material and proportional to the force exerted upon the material. In some instances, a material may undergo plastic deformation and still remain substantially elastically deformable. For example, the metal insert of ordinary surgical masks may be plastically deformed to conform to the contour of the nose bridge of the wearer. After plastic deformation, however, the metal insert retains a certain level of elasticity that mitigates any potential discomfort to the wearer.

The term "epidermis" means the skin and refers to the membranous protective covering of the body consisting of the epidermis and corium.

The term "measurement region" or "measurement site" as used herein refers to a region of tissue in which the physiologic parameter is measured. Typically, but not necessarily, the measurement region is adjacent to the tissue contacted by the probe of the inventive device or in the case where the probe is placed on the epidermis, the measurement region is below the probe.

The term "mucosal surface" as used herein refers to a surface of mucous tissue containing or associated with mucus secreting glands, and which lines body passages, tubular structures, and organs. The mucosal surfaces of interest herein include, but are not limited to, the sidewall of the nares, cheek, and mouth of a patient.

The term "nonepidermal surface" as used herein encompasses all mucosal surfaces and also includes the surface of any tissue that does not pertain to the epidermis.

The term "patient" as used herein means a mammalian subject, preferably a human subject, that has, is suspected of having, is or may be susceptible to a condition associated with the analyte, or is in need of analyte measurement.

The term "perfusion failure" as used herein means a reduction in blood flow associated with maldistribution of blood through the circulatory system and a reduction in blood flow to a less critical tissue and/or organ relative to blood flow in vital (critical) tissues and organs (e.g., the brain and heart). The term "perfusion failure" is also clinically termed "circulatory shock." In general, "perfusion failure" is meant to encompass reduction in blood flow associated with an increase in $pCO_2$ significantly above $pCO_2$ associated with normal perfusion.

The term "physiologic parameter" as used herein refers to one of a set of measurable factors that is indicative of biological process of a living organism. For example, a physiologic parameter may be the presence or the concentration of a chemical analyte within a tissue. As another example, the physiologic parameter may be flow rate of blood in a tissue. Optionally, the physiologic parameter may be used to determine a systemic or regional condition. Physiologic parameters may be categorized as metabolic, respiratory or mechanical.

The term "sensing site" means the site where the device of the present invention is placed to obtain the tissue measurement. The sensing site may be the epidermis or the sensing site may be a tissue, such as the mucosa, that is adjacent to the measurement region.

The term "tissue" as used herein refers to an aggregation of morphologically similar cells and associated intercellular matter acting together to perform one or more specific functions in the body. The term also applies in a wider sense to all materials differing in structure and function, which go to make up an organ. Tissue includes epithelium; connective tissues, including blood, bone and cartilage; muscle tissue; and nerve tissue.

The Inventive Device:

The present invention provides for contacting an epidermal or nonepidermal surface of a a patient's body to determine a physiologic parameter of the patient. The physiologic determination may be made using trans-tissue or intra-tissue measurements in order to determine a systemic or regional condition. The device includes a sensor responsive to the physiologic parameter. Typically, but not necessarily, the sensor is placed on a sensing site adjacent to a measurement region of the tissue, is responsive to an analyte associated with the physiologic parameter, and is at least partially contained in a probe. A means may be provided for reducing interference at the sensing site or in a sensing area of the device. Such means may represent an integral portion of the probe. In addition, the device may be placed in contact with a surface within a patient's body or on a patient's body in order to carry out analyte detection. To ensure that contact between the device and the body surface (interior or exterior) of the patient does not compromise the accuracy and/or precision of analyte measurements, a means may be provided for preventing application of excessive pressure to the region such that blood flow to the body tissue is not disturbed. In addition or in the alternative and depending on the sensing site where the probe is placed, the probe may be constructed to allow the sensor to be secured to the sensing site without relying solely on an adhesive. The sensor may optionally include a holding means, such as a clip, an adhesive, a gel, and other such suitable means. Preferably, the device further comprises an indicating means operably connected to the sensor for indicating the analyte quantity or concentration in the tissue of the patient.

It should be noted that the inventive device may be used to measure the chemical analyte concentration at epidermal as well as nonepidermal surfaces. Further, the inventive device may be used to obtain an indication of systemic or global perfusion as well as regional perfusion. For systemic or global perfusion, the device is placed against mucosal surfaces, but in some instances, the device may be placed against skeletal muscle as well as certain internal organs whose metabolic activity is affected during systemic or global perfusion. The inventive device may also be used on epidermal surfaces, such as the skin, to measure regional perfusion and assess global perfusion therefrom provided that the regional perfusion measurement is taken at a suitable location. For example, global perfusion cannot be assessed from a regional perfusion measurement on the finger because the body can change the regional perfusion in the fingers for a variety of reasons other than reduced global perfusion. However, measurements taken on the body trunk (or under the tongue) are ideal location because there are very few reasons why perfusion would be compromised other than lack of global perfusion.

In addition, the inventive sensor may be employed to detect analyte in tissue of critical organs such as the heart with respect to non-perfusion applications. Examples of mucosal tissue where analytes may be measured with the inventive device include, but are not limited to the interior surfaces of the mouth (e.g., buccal and sublingual regions), nares, esophagus, stomach, rectum, and intestines. For regional perfusion, the device may be placed against limbs, such as arms and legs, as well as internal organs such as the heart, liver, and kidneys.

Figure 1B:
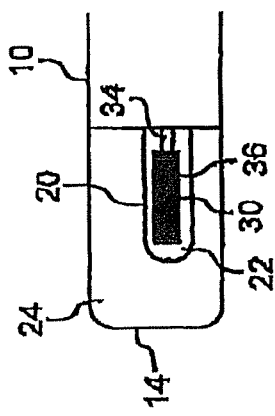

The invention is described herein with reference to the figures, in which like parts are referenced by like numerals. The figures are not to scale, and in particular, certain dimensions may be exaggerated for clarity of presentation. FIG. 1, for example, shows an embodiment of the inventive device having an elongate probe 10 containing a sensor 30. As shown, the probe is generally elliptically shaped and has two ends, a proximal terminus 12 and a distal tip 14. Located at the distal tip 14 is a perpendicularly oriented interference-reducing means in the shape of a recess 16 that substantially defines device sensing area 18 and is integral with the elongate probe 10. An analyte-sensitive portion 36 of the sensor 30 is located within the device sensing area 18. Optionally, as shown in FIG. 1, the analyte-sensitive portion 36 of the sensor 30 may be located in a depression or cowl 20 in the device sensing area 18. The interior of the cowl 20 represents "dead space that communicates with the exterior of the probe 10 through opening 22 of a contact surface 24 of the cowl 20. The sensor 30 extends by way of portion 34 along the elongate axis of the probe 10 and terminates at the proximal terminus 12, forming a sensor transfer means such as connector 32 for operative connection with an indicating means 40. The connector 32 may carry electrical, optical, or another type of signal to the indicating means 40. The indicating means 40 may then interpret the signals from the connector 32 and then convert the signals into an analyte concentration that, in turn, can be displayed to the user. As shown, the probe 10 also includes an optional deformable region, indicated at 26, composed of a flexible material that allows for elastic deformation in response to a force.

FIG. 2 illustrates various probe and sensor configurations of the inventive device. While the configurations illustrated in FIGS. 2A-2D are generally useful for trans-tissue analyte measurements, FIG. 2E illustrates a configuration useful for intra-tissue measurements. For example, FIG. 2A illustrates a device having a sensor 30 contained in the cowl 20 of a probe 10 that is substantially cylindrical in shape. In such a case, the interior of the cowl, i.e., the dead space, represents the device sensing area 18. FIGS. 2B and 2C illustrate that the inventive device may include an optional membrane 28 over the cowl opening 22, the membrane chosen to selectively allow analyte to be transmitted therethrough. FIG. 2D illustrates a device that exemplifies instances where no dead space is required. These and other components of the inventive device, as well as how they interrelate, are discussed below in greater detail.

Holding Means

In general, it is preferred that analyte measurement takes place when the device is substantially immobilized to allow for an accurate measurement to be taken in the tissue in which analyte measurement is desired. Thus, the inventive device may include an optional holding means. For example, as shown in FIG. 1, an optional holding means in the form of a clip 50 is attached to the probe 10 between the proximal terminus 12 and the distal tip 14. The clip 50 is generally L-shaped. That is, the clip 50 is formed from a shorter straight portion 52 and a longer straight portion 54 that meet at a curve 56 of about 90.degree. The shorter portion 52 extends generally perpendicularly from the probe 10 in the same direction as the cowl 20, and the longer portion 54 is generally parallel to the probe 10. As a result, the probe 10 and the clip 50 generally form a U-shape, wherein the tip 58 of the clip is closest point on the clip 50 to the distal tip 18 of the probe.

Through clamping action between the probe contact surface 24 and the clip contact surface, indicated at 60, the U-shape serves to secure the probe 10 immovably adjacent a surface of patient tissue. This particular clip is well suited for use with devices for measuring analyte in an interior surface of a cheek of a human patient, as such the clamping action of the clip on the exterior cheek surface may hold the device in place. That is, the clip contact surface 60 is placed in contact with an exterior surface of the cheek and the probe contact surface 24 is placed in contact with the interior of the cheek.

Figure 2A:
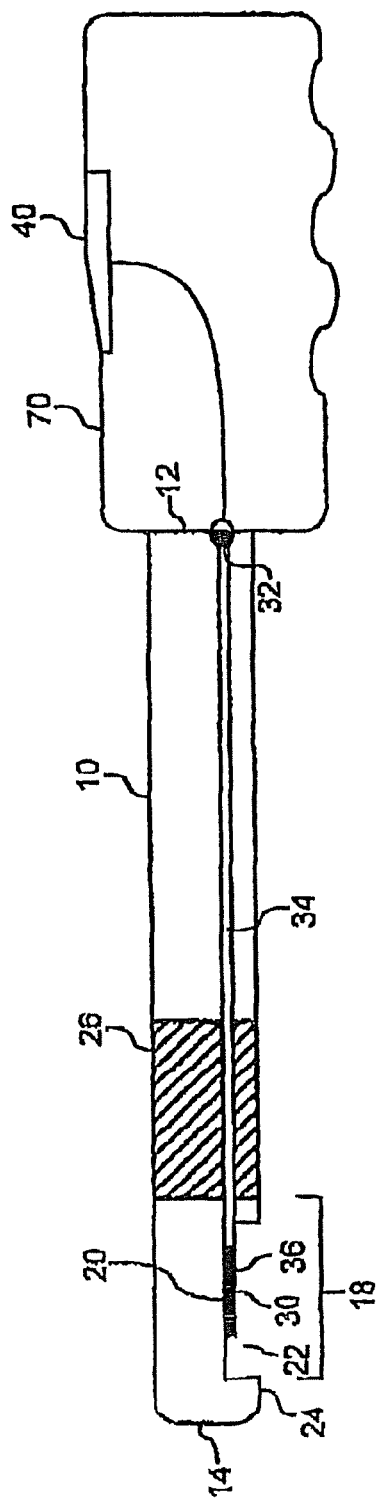
FIGS. 2A-2E, collectively referred to as FIG. 2, illustrate various probe and sensor configurations of the inventive device.

FIG. 3 illustrates devices similar to that illustrated in FIG. 2A in conjunction with a number of different clips. FIG. 3A, for example, illustrates a device that includes a clip 50 similar to that illustrated in FIG. 1 except that the clip includes a loop 62 that may serve as a spring mechanism of a means for preventing blanching as discussed below. One disadvantage of this clip is that the clip has a relatively small contact surface area. As the effectiveness of the clamping action sometimes requires a large surface area, FIG. 3B illustrates another version of a clip 50 illustrated in FIG. 3A, except that a contact surface 60 having a larger area is provided to improve clamping action. As discussed below, the larger contact surface area may also decrease blanching.

The holding means may also comprise an adhesive (not shown) or gel, which may be used alone or in conjunction with a clip. When used in conjunction with a clip, the adhesive or gel is provided on contact surface 60 to enhance immobilization. When used alone, i.e. no clip is used, the adhesive or gel may be provided on surface 24, as best seen in FIG. 1.

FIG. 3C illustrates another example of a device having a clip 50 that includes a loop 62 except that the tip 58 of the clip extends away from the tip 14 of the probe 10. As shown, the distance from the contact surface 60 to the sensor 30 is indicated by L. Typically, L is equal to or greater than 1 cm. Preferably, L is at least 3 cm. This because the clip 50 contacts the tissue at a distant location from the sensor 30, any blanching of the tissue occurs away from the sensor. As a result, blanching of the tissue under assay is avoided. FIG. 3D illustrates an example of a device that includes a clip 50 similar to that illustrated in FIG. 3A, except that the clip has a protrusion extending therefrom that serves as a handle 64 to allow a user to pull the tip of the clip away from the probe.

The optimal combination of design options for a clip, such as whether to incorporate curvature and handles, may be determined in view of the teachings provided herein and/or through routine experimentation. For example, any clip may have a handle extending therefrom. In addition, the shape of the holding means may also correspond to the region of intended use. For instance, the device shown in FIG. 3A is suitable for analyte measurement in cheek tissue (as discussed above) or another tissue flap, whereas the device shown in FIG. 3C may be more suitable for a sublingual location. When the analyte measurement is performed within the mouth, the device may be clamped to the chin to mitigate blanching. In addition, if a clip is employed as a holding means, it is not necessary to attach the holding means to the probe; the holding means may be a separate component from the device. As shown in FIGS. 1 and 3, the clip 50 is attached via a clip connector 51. The clip may, however, be attached to the device at any location such as the probe, handgrip, cable, or other location that does not interfere with the proper functioning of the device.

In order to substantially immobilize the device adjacent to a surface of tissue for analyte measurement, other holding means suitable for use with the inventive device, include, but are not limited to, fasteners, straps, belts, hooks, clamps, clips, sutures, staples, adhesives, gels or other known means, alone or in combination.

In the alternative, a holding means may be omitted when the device is constructed for hand held applications. As illustrated in FIG. 2A, the probe 10 may be constructed to allow the sensor to be held adjacent to or on a surface by the user. Optionally, the probe 10 may be constructed with a grip 70 for facilitating probe manipulation and positioning. As shown, an indicating means 40 is located in the grip 70 and operatively connected to the sensor 30. In addition, the grip may be contoured to conform to that of a human hand. Furthermore, the grip may have a textured surface or may be otherwise made non-slipping by proper placement of appropriate non-slipping materials. Design parameters relating grip design can be learned through routine experimentation by one of ordinary skill in the art.

Means for Preventing Application of Excessive Pressure

As discussed above, the inventive device may be employed to determine the quantity or concentration of a chemical analyte within a measurement region of a body tissue. However, the concentration of certain analytes may be altered depending on the fluid flow to the tissue or the amount of fluid in the tissue. That is, when fluids such as blood are occluded from living tissue, biological processes that normally take place in the tissue are disrupted. If it is desirable to measure the quantity or concentration of analyte that is produced by the biological process, occlusion of fluids would skew analyte measurements. For instance, blanched tissue tends to exhibit abnormally high $CO_2$ and low $O_2$ concentrations as well as reduced blood flow. Thus, for accurate measurements of analytes such as $O_2$ in tissue, blanching must be avoided. Accordingly, where fluid amount or flow affects the accuracy or precision of analyte measurement, the inventive device also includes a means for preventing excessive pressure of the measurement region such that blood flow to the tissue being measured is not substantially occluded.

Blanching is caused by excessive pressure applied to a tissue, and pressure is the quotient of force over area. Accordingly, there are at least three approaches to reduce pressure to a region of tissue: to increase the surface area to which force is applied; to decrease the amount of force applied; and to ensure that any pressure is applied away from the region. To prevent the probe from substantially blanching the tissue during its use, the probe is constructed such that the contact area of the probe serves to evenly apply the force (clamping or otherwise as described above) needed to render the sensor immobile with respect to the sensing site. Thus, the contact surface should have no sharp protrusion(s) such as corners that may locally intensify the pressure applied to the sensing site. In other words, it is preferred that the profile of contact surface is smooth and/or rounded rather than angular or jagged. In addition, the contact surface should have the largest area practicable to distribute the applied force and to reduce the pressure applied at any point. Because nonepidermal surfaces, such as mucosal surfaces, are particularly suitable for measurement of internal concentration of gas analytes, the largest practicable area may be limited by the overall size of the probe if the probe is sized to fit, e.g., into the nares, mouth, or cheek of the patient. Small sensors, small measurement regions, and small isolating means are generally desired because the small overall size of the device may allow the device to be used in more locations within a patient. The area of contact between the sensor and the tissue adjacent to the measurement region is typically about 1 $cm^2$ to about 6 $cm^2$, preferably about 1 $cm^2$ to about 2 $cm^2$.

Similarly, the weight of the device is also a factor to consider with respect to blanching since excessively heavy devices may result in higher pressure applied to the tissue within which analyte concentration or quantity is to be determined. Lightweight devices are preferred over heavy devices. Typically, the inventive device should not exceed about 250 g, the preferred weight of the device being about 1 g to about 100 g.

There is generally more variability associated with handheld devices than with devices that employ a holding means. Because a holding means may be used to immobilize the inventive device with respect to tissue in a substantially reproducible manner, a device having a holding means is preferred over one without to avoid errant blanching. Thus, while a holding means is not critical to the invention, it is preferred that the inventive device include a holding means to provide greater control in lessening tissue blanching.

The holding means may be arranged with respect to the sensor such that deployment or application, in the case of adhesives or gels, of the holding means does not result in the application of excessive pressure at the measurement region. To illustrate, the clip 50 of the device of FIG. 3A tends to apply pressure to the region of body tissue in which analyte is measured because the bulk the immobilization force is applied at the contact surface 60 at or near the tip 58 of the clip 50. However, the clip 50 of the device illustrated in FIG. 3C is designed such that the bulk of immobilization force is applied away from the region of body tissue in which analyte is measured. That is, the bulk of force applied by the clip is at contact surface 60 located nearer to the middle of the probe than the tip 14 of the probe. Thus, the clip illustrated in FIG. 3C represents a holding means that immobilizes the probe such that pressure is remotely applied to a patient. In the alternative, when adhesives or gels are used, alone or in combination with a clip, very little additional force is applied.

Figure 5:
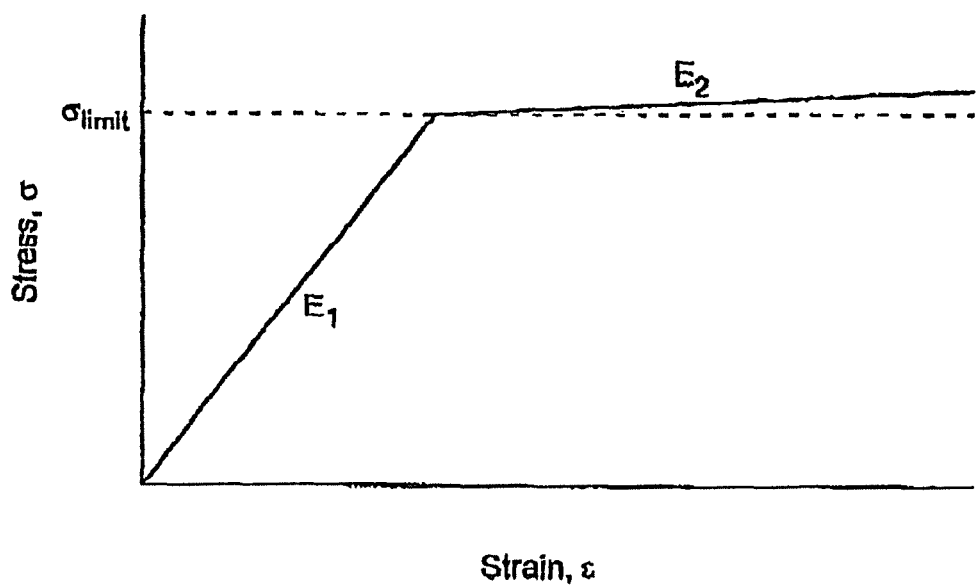
FIG. 5 illustrates an idealized stress-strain curve for a material that exhibits optimal elastic properties for use in the device of the invention.

Certain construction considerations may be employed in both handheld devices and devices to lower the potential of tissue blanching during use. For example, at least a portion of the inventive device may be composed of a deformable material. Preferably, the material is elastically deformable. Optimally, the material is selected to exhibit a constant elastic modulus for a stress imposed upon the material up to an upper stress limit; for a stress above the upper limit, the elastic modulus is much lower. FIG. 5 illustrates an idealized stress-strain curve for the optimal material. For stresses up to $\sigma_{limit}$, the slope of stress to strain is shown as modulus $E_1$. However, for stresses greater than $\sigma_{limit}$, the slope of stress to strain is shown as modulus $E_2$. As illustrated, $E_2$ is less than $E_1$; $E_2$, while positive, is close to zero. Materials exhibiting this type of elastic behavior allow a device to be constructed to avoid excessive pressure applied to tissue to which the probe is adjacently secured. The deformable material may be any suitable polymer, such as one selected from, but not limited to, the group consisting of polyethylene, polypropylene, polybutylene, polyamide, polyimide, polyester, perfluorinated polymer, polystyrene, poly (vinyl chloride) and elastomers such as rubbers and silicones. It should also be noted that materials that do not exhibit this type of elastic behavior are not necessarily precluded from use in device construction.

Thus, a portion of the inventive device may be composed of a deformable material as described above. For instance, as shown in FIG. 1, to control the pressure applied to a tissue surface such that the tissue is not substantially blanched, the probe 10 may include a deformable region 26 that is composed of the deformable material as described above. Depending on the desired performance of the device with respect to the blanching, the deformable region may represent a portion of the probe near the probe tip 14, as illustrated in FIG. 2 or near the probe terminus 12, as illustrated in FIG. 3. The size and shape of the deformable region is controlled by the mechanical properties to mitigate tissue blanching. The holding means or a portion thereof may be constructed from such an elastic material as well. Thus, as shown in FIGS. 1 and 3, at least a portion of the clip 50, i.e., a deformable region 63, may be composed of the deformable material as described above. Similarly, the positioning and the size of the deformable region may be controlled by the desired degree of blanching prevention.

As another option, a compliant material may be employed to more uniformly distribute pressure applied to a tissue surface by the device. That is, one or more pads composed of foam, rubbery, gelatinous, and/or other compliant materials may be included in the device where the device contacts a patient's tissue to distribute pressure more uniformly and to lessen the potential for tissue blanching. Such pads may be interposed between a tissue surface and the contact surface of any of the probes and/or clips. Such compliant materials may also provide improved sealing for an isolating means as discussed below. Polymeric materials that exhibit sufficient compliancy include, but are not limited to, silicones, butyl rubbers, and urethanes.

It is important to note that material selection alone may not be enough to ensure proper pressure control. For example, the extent of deformation needed to ensure proper pressure is a function of both elastic modulus of the material as well as the overall geometry and size of the elastic material. Thus, the dimensions of the device may be appropriate for a spring-like pressure-release mechanism. In the alternative or in addition, a spring mechanism may be included to control the pressure applied to the tissue surface by the probe. The spring mechanism may be incorporated as a part of the probe or as a part of the holding means. As shown in FIGS. 3A-3D, loop 62 of the clip serves as a spring mechanism to ensure that excessive pressure is not applied to the measurement region of the tissue. In any case, it is within the capability of one of ordinary skill in the art to construct the device, through material selection or spring construction, for example, such that the pressure applied to any surface contacted by the device does not exceed a predetermined limit. Applicants have constructed an embodiment of a device that can be secured immovably adjacent to a surface without applying a pressure exceeding about $1.5 \times 10^4$ pascals to the surface using such a spring mechanism.

As discussed above, the shape of the device may contribute to the deformation behavior of the inventive device in order to prevent application of excessive pressure. For example, wall thickness, aspect ratio, couplings, and/or linkages may be selected in either the probe or holding means design to control deformation in response to a force. That is, a portion of the probe or the clip may have mechanical features such as indentations, thinner wall thickness, smaller diameter, or joints that restrict the pressure applied to the tissue under the probe when forces are exerted on the non-sensing end of the probe. Thus, as illustrated in FIG. 3B and FIG. 3D, at least a portion of the clip indicated at 66 may be shaped to allow increased or decreased rigidity. For example, the clip illustrated in FIG. 3B includes a perforated section 66 in order to provide a more easily deformable section to ensure that deployment of the inventive device does not result in the application of excessive pressure to tissue. Similarly, the clip illustrated in FIG. 3D includes bellows-like pleats 66 that serve to mitigate the likelihood of undesirable tissue blanching. Thus, it should be evident that one of ordinary skill in the art may be able to shape the clip to ensure a proper level of deformation in response to a force. And as noted, adhesive, gels, sutures, and other types of fasteners may be used in lieu of clips to prevent tissue blanching and the application of force.

Means for Reducing Interference

Depending on the desired analyte measurement and the sensor employed to carry out the analyte measurement, a means for reducing interference may be required. Such means may be constructed to reduce interference from any of a number of sources. For example, such means may be used to reduce interference from electromagnetic radiation or a gaseous or liquid fluid. When the inventive device is employed to determine the quantity or concentration of a gaseous analyte in a body tissue, the device may include an interference-reducing means in the form of an isolating means for inhibiting airflow around the sensor. Such an isolating means allows gaseous analyte from the tissue to come to equilibrium in an area adjacent to the measurement region. In turn, the isolation means allows the inventive device to be employed to determine the quantity or concentration of a gaseous analyte in a patient's tissue.

While the inventive device may be employed to determine the quantity or concentration of analyte for any of a number of different types of tissues, the operation of an ambient isolation means by way of an example is hereby described as it relates to the measurement of a gaseous analyte in a patient's cheek tissue. Because gas diffusion necessarily takes place at a faster rate in a gaseous medium than in a solid medium, any difference in partial pressure of a particular gaseous analyte between the inner surface of the cheek and interior of the mouth, as the sensing site for example, will result in a partial pressure gradient within the cheek tissue. Without a barrier, the partial pressure of gaseous analytes at the surface of the cheek is approximately equal to that within the mouth. However, when gas is prevented from dissipating from the cheek surface, the partial pressure of the gas at the surface of the tissue equilibrates with the partial pressure of the gas in the interior of the tissue. Thus, by measuring the partial pressure of a gaseous at equilibrium, the quantity or concentration of the analyte within the tissue can be determined.

Using the buccal surface as an example of the sensing site and referring to FIG. 1, recess 16 in combination with cowl 20 represents a type of isolating means for inhibiting airflow around the sensor. Placing the cowl 20 immovably adjacent to an inner cheek surface such that the contact surface 24 forms a seal about opening 22 with the cheek surface allows analyte gas to enter sensing area 18 through opening 22. In other words, cowl 20 in recess 16 is an integral portion of the probe that traps gaseous analyte in sensing area 18 and prevents the analyte from dissipating into the interior of the mouth. Optionally, a pad or skirt of compliant material (not shown) may be provided around the perimeter of opening 22 to enhance sealing of the sensing area and prevent dissipation of the analyte.

After sufficient time for the partial pressure of the gaseous analyte within sensing area 18 to reach equilibrium, the sensor 30 within region 18 will be exposed to the analyte at the same partial pressure as the analyte within the cheek tissue. The volume of dead space will determine the time needed for the concentration of an analyte within the region to come to equilibrium with the concentration of analyte with the tissue. Because a smaller volume of dead space results in faster equilibration, it is preferred that the dead space about the sensor does not exceed about 10 $mm^3$, or more preferably, that the volume of dead space does not exceed about 1 $mm^3$. In some cases, as is with the device illustrated in FIG. 2D, substantially no dead space is required. Once immobilized and secured in place, any version of the device may be adapted to make single, multiple, or continuous measurements of the concentration of analyte within sensing area 18. Thus, the inventive device may be adapted to detect or measure analyte concentration within a tissue or monitor changes in analyte concentration within a tissue. The analyte detection and/or measurement may be carried out in combination with or using predictive algorithms and end-point verification techniques known in the art. Sensor response time, of course, plays an important role in such detection and measurement.

The ambient isolating means for inhibiting airflow around the sensor should be selected from a class of materials that exhibits low gas diffusivity as well as low gas absorption to act as a gas barrier to the surrounding environment. However, many elastomers have high gas diffusion rates and high gas absorption. Therefore, the probe or the isolating means may be formed from a plurality of materials to form a composite or laminate structure. For example, a material can be coated with a suitable material that provides adequate barrier properties to prevent gaseous analytes from diffusing therethrough. Materials known to have low permeability to gas include, but are not limited to, metals (e.g., aluminum, tin), ceramics (e.g., silicon dioxide, titanium nitride), and certain polymeric materials (e.g., high-density polyethylene, parylene).

Figure 2B:
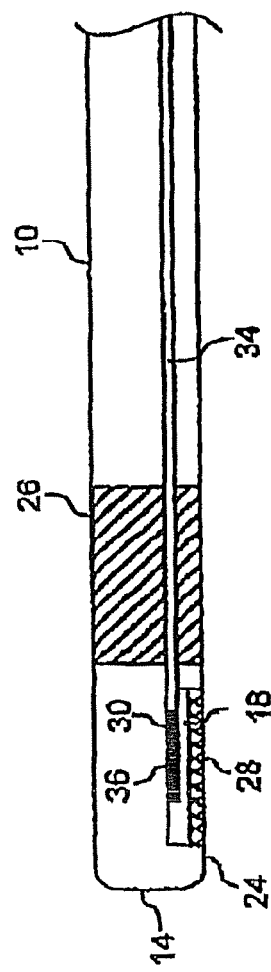
Figure 2C:
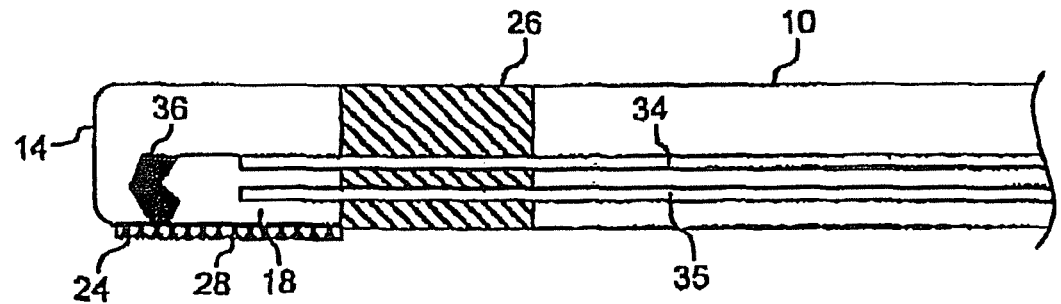
Figure 2D:
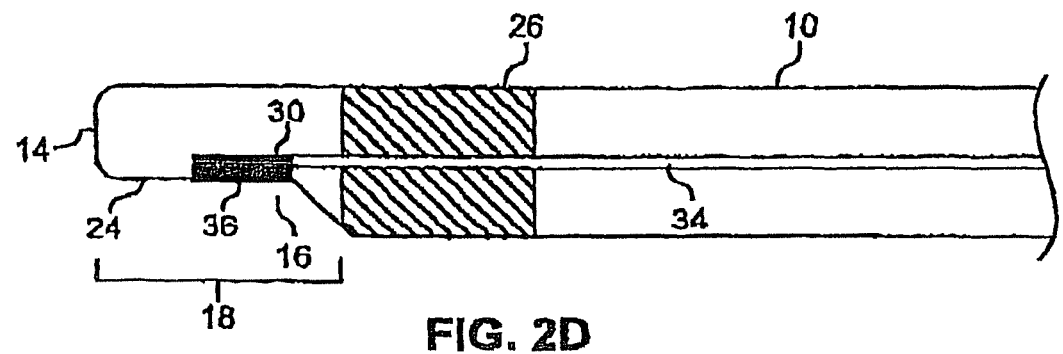

In addition to airflow, there are other possible sources of interference that may compromise the performance of the inventive device. Depending on the particular sensor used and the location of the sensing site, certain bodily fluids or ambient air may interfere with the accuracy, precision, and/or response time of the sensor. For example, when the inventive device employs a light-sensitive sensor and is placed for an extended period of time within a body cavity that contains a bodily fluid, the sensor may contact the bodily fluid. The optical properties of the bodily fluid may be such that they alter the amount of light reaching the sensor. Thus, the means for reducing interference may also include a selectively permeable barrier or membrane that allows the analyte and optionally noninterfering compounds to reach the sensor while preventing moieties that may interfere with sensor measurements from reaching the sensor. Similarly, when the accuracy of certain sensors is sensitive to pH, a means for reducing pH interference may be provided. Furthermore, if interstitial bodily fluids will tend to interfere with the measurement of a gaseous analyte, a membrane permeable to the gaseous analyte but impermeable to interstitial bodily fluids may be provided as a part of the inventive device wherein the membrane is interposed between the sensor and the tissue in which the analyte is measured. Such a membrane may be provided as at least a portion of detachable sheath as illustrated in FIG. 7, an integrated portion of the device as illustrated in FIGS. 2B-D or in any other form known sufficient to protect the sensor from exposure to an interfering moiety as discussed herein.

The Sensor

The sensor of the invention is selected according to its sensitivity or response to analyte concentration. The sensor may be responsive to analyte concentration through a chemical reaction with a reactant, through absorption, emission or modification of electromagnetic radiation, through generation or alteration of electromagnetic radiation, or through a combination of any of the above. For example, $CO_2$ sensors may operate by detecting a chemical reaction with a reactant in response to change in pH in the sensor environment. Specifically, such sensors have a membrane that is permeable to $CO_2$ and separates a sodium bicarbonate or carbonic acid ($H_2CO_3$) solution from the environment. A pH sensor in the device measures the pH of the sodium bicarbonate solution. Microelectrode, Inc. manufactures an exemplary CO2 sensor of this type.

In addition, a number of different types of optical sensors may be employed in the present inventive device. For example, conventional calorimetric and fluorimetric optical sensors for $CO_2$ are known in the art. Such sensors have been incorporated into plastic film $CO_2$ sensors, such as those described in U.S. Pat. No. 5,480,611 to Mills et al. Generally, such $CO_2$ sensors rely upon pH changes induced in an aqueous solution upon its exposure to different levels of $CO_2$ and utilize a pH-sensitive dye to provide a qualitative and/or quantitative measure of the extent of the change in pH and, therefore, the change in $CO_2$ concentration. These sensors have similar design features such as those that involve the encapsulation of a pH-sensitive dye, either in a thin aqueous solution or fixed on an inert support. Optionally, these sensors include a fiber optic system for delivery and return of the essential light components.

When a fiber optic system is employed, the sensor may include a single optical fiber. Structures, properties, functions, and operational details of fiber optic chemical sensors can be found in various patents and publications such as those listed in U.S. Pat. No. 6,071,237 to Weil et al. Such optical sensors may be adapted for use in monitoring a patient's arterial oxygen saturation level, as described in U.S. Pat. No. 5,111,817 to Clark et al., or for use in monitoring $pCO_2$, as described in U.S. Pat. No. 5,714,121 to Alderete et al. An optical sensor 30 for detecting an analyte, for example, may be composed of a single optical fiber 34, as shown in FIG. 2A having an analyte-sensitive portion 36 at one end and, at the other end, a connector 32 for communication with indicating means 40.

The analyte-sensitive portion 36 contains an indicator solution having a suitable analyte-sensitive indicator component, generally a fluorescent dye, and substantially no air. Examples of fluorescent dyes include without limitation fluorescein, carboxyfluorescein, serninaphthorhodafluor, seminaphthofluorescein, naphthofluorescein, 8-hydroxypyrene 1,3,6-trisulfonic acid, trisodium salt ("HPTS"), and dichlorofluorescein, with HPTS particularly preferred. In operation, light of a predetermined wavelength is directed from an external source (not shown), through the optical fiber 34, impinging on the encapsulated indicator composition in the analyte-sensitive portion 36 which is exposed to the analyte at equilibrium with the analyte concentration in the patient's tissue. As a result of interaction with light and the analyte, the indicator composition emits fluorescent light that returns along the fiber 34. The intensity of the fluorescent light is related to the concentration of analyte. The emitted light is carried to the connector 32 to be detected and converted electronically to an analyte concentration value as indicated by the indicating means 40. This type of sensor, as with all Severinghaus-type $pCO_2$ sensors, however, may require that the indicator composition be maintained at a particular moisture level that may not be required by the infrared sensors as described above. Moreover, if the Severinghaus-type sensor is contacted with the tissue, it is important that the osmotic considerations are taken into account so the bicarbonate concentration within the sensor is maintained. It is has been found that osmolality in the mouth is about 25% of normal and that osmolality elsewhere for nonepidermal tissue is about 100% of normal.

As an alternative, a probe of a preferred embodiment may contain an infrared sensor using a non-dispersive infrared (NDIR) technology. One example of such a sensor is described in U.S. Pat. No. 5,423,320 to Salzman et al. This patent describes an infrared light source coupled to a first infrared light transmissive optical fiber. As illustrated in FIG. 2C, infrared light is transmitted from the light source through the optical fiber 34 and to a gas sensing area 18 of the sensor that contains gas that is to be analyzed. The light is allowed to interact with the analyte before an infrared reflector 36 within the region directs the infrared light emitted from the first optical fiber 34 into a second optical fiber 35 that is coupled to an infrared detector. Alternatively, a single optical fiber could be used if an optical splitter means were also deployed to separate the emitted energy from the excitation energy. The signal detected by the detector is compared with the signal generated by a known calibration level to produce an output that indicates the level of analyte in the sensing area. Both oxygen and carbon dioxide, as well as other gases, can generally be measured with a NDIR technique. Some gases may be affected by the presence of other gases, and compensation may be required.

Salzman et al. also describes that $pCO_2$ and $pO_2$ may be measured using a Severinghaus electrode based $CO_2$ sensor and a Clark electrode $pO_2$ sensor, respectively, each of which can be used in the present invention as well. Where a Severinghaus electrode is used in place of an infrared sensor, electrical signal lines are used in place of fiber optics, and an external electrical signal generator is used in place of the infrared light source. The construction of various Severinghaus-type sensors are known in the art, one example of which is described in Vurek et al. (1983), "A Fiber Optic $PCO_2$ Sensor," Annuals of Biomedical Engineering, 2:499-510.

Figure 2E:
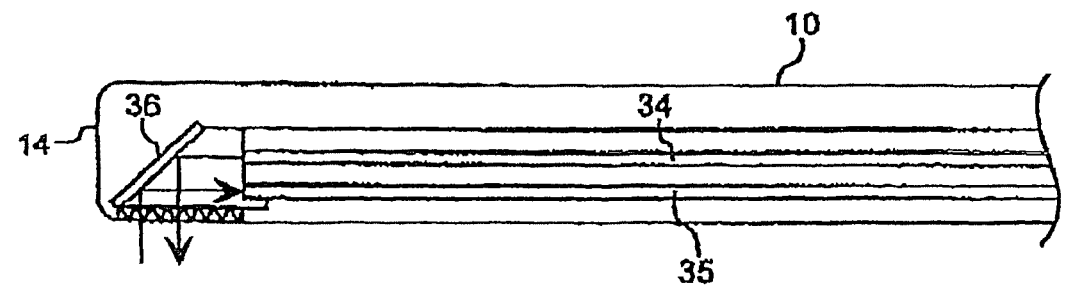

In addition, optical or other types of sensors may be used to engage in intra-tissue determination of a physiologic parameter of a patient. As depicted in FIG. 2E, the inventive device may include two optical fibers, indicated at 34 and 35. Probes including optical fibers are well suited for taking tissue measurements when the sensing site is the epidermis. Electromagnetic radiation is transmitted through the optical fiber 34 and reflected by a reflector 36. As a result, the radiation is redirected into a tissue, which may be below the surface of the skin. The radiation is allowed to interact with the analyte in the tissue before returning to the reflector and 34 into a second optical fiber 35 that is coupled to a detector.

As another alternative, or in addition to, an optical sensor adapted to generate a precise quantitative value of an analyte concentration, the sensor may be employed to provide a generalized qualitative indication of the analyte concentration. This type of sensor may, for example, employ calorimetric indicators such as those used in litmus strips or those used in home pregnancy tests. Such sensors would provide the user an indication of whether an analyte is present and/or the range of the analyte concentration detected. In addition, such a sensor may be constructed inexpensively and thus may be treated as disposable, irrespective of whether the probe containing the sensor is disposable. In the case wherein any component of the sensor undergoes an irreversible reaction to provide an indication of an analyte concentration, the sensor may be adapted for single use applications. Reversible reactions may be employed for both single and multiple use applications. Notably, reversible reactions should be take place at a sufficiently slow rate to allow a user to take notice of the sensor response. This means that response should be observable by a user for at least 15 seconds, preferably for at least 30 second to 1 minute, optimally 1 to 5 minutes.

Figure 6A:
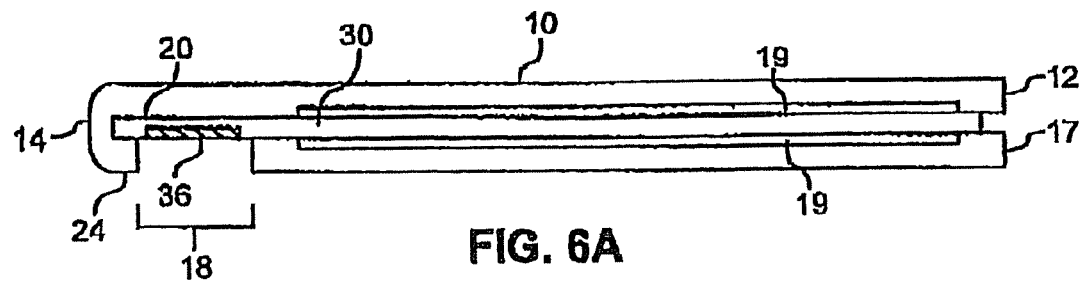
FIGS. 6A-6D, collectively referred to as FIG. 6, illustrate versions of the inventive device that may be employed to provide a general indication of the concentration of an analyte within a region of a body tissue.

FIG. 6A illustrates a probe 10 containing a sensor 30 which may be employed to provide a general indication of the concentration of an analyte within a region of a body tissue. The probe 10 is similar in construction to that illustrated in FIG. 2A and has a cowl 20 as an isolating means that substantially defines sensing area 18. An analyte-sensitive portion 36 is located near the proximal terminus of the sensor 30 and is responsive to the analyte concentration. The probe 10 and the sensor 30 may be constructed to ensure that the sensor 30 is immobilized with respect to the probe 10 during analyte measurement. That is, the sensor may be detachably or nondetachably coupled to the probe. Such coupling may involve, for example, providing mating surfaces, fastening means, locking mechanisms, or other means known to one of ordinary skill in the art for detachable or nondetachable coupling. For example, as illustrated in FIG. 6A, the sensor 30 is slid or inserted into an opening 17 at the proximal terminus 12 of the probe and thus into a cavity 19 of the probe 10 shaped to provide sufficient friction to hold the sensor 30 in place. The analyte-sensitive portion 36 of the sensor 30 is thus placed in the sensing area 18 of the probe 10 so as to ensure that the performance of the analyte-sensitive portion 36 is not compromised by ambient interference.

Figure 6B:
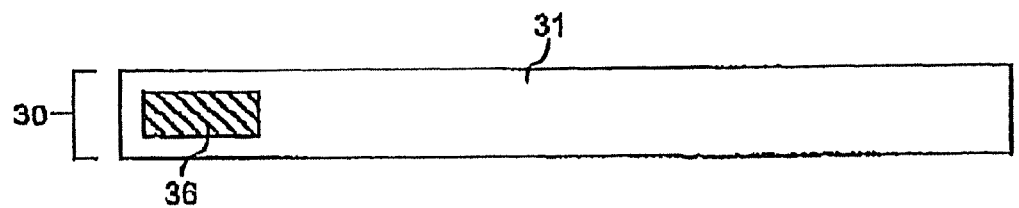

As shown in FIG. 6B, the sensor 30 comprises a substrate 31 having an analyte-sensitive portion 36 thereon. The substrate 31 is a planar solid member but may be constructed in a number of other shapes including, for example, cylindrical, conical, spherical, rhomboidal and cubic. In addition, the analyte-sensitive portion may be constructed, for example, in the shape of a square, rectangle, circle, oval, or cross.

Figure 6C:
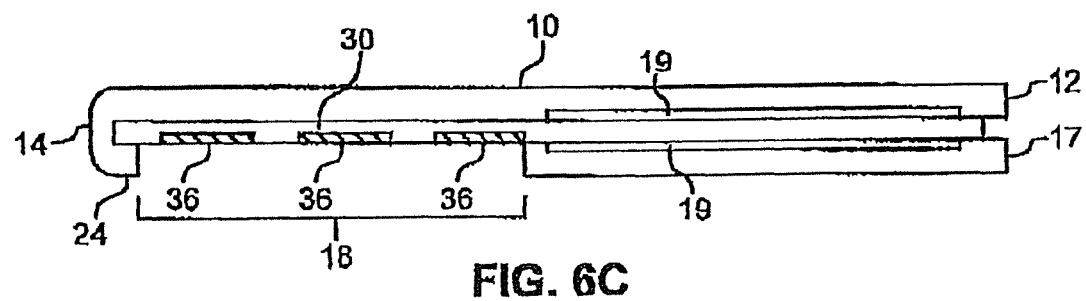
Figure 6D:
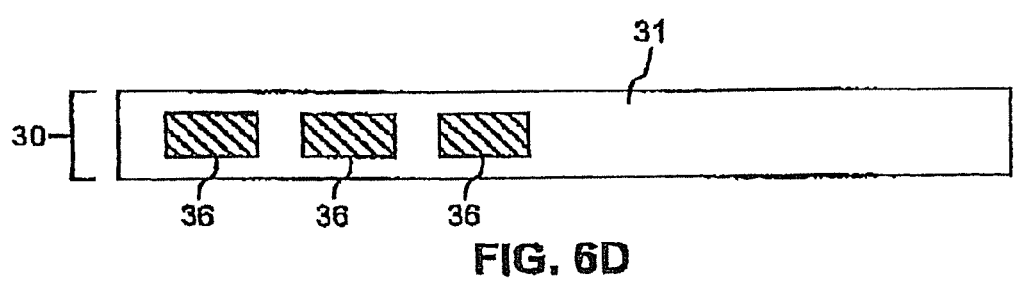

As illustrated in FIGS. 6C and 6D, a probe 10 may contain a sensor 30 comprising a plurality of analyte-sensitive portions 36 on a substrate 31, each analyte-sensitive portion responsive to a different analyte or analyte concentration range. The plurality of analyte-sensitive portions may be associated with one or more sensors, and analyte-sensitive portions may be isolated from each other. For example, if a plurality of analyte-sensitive portions is provided in response to a different analyte, each of the portions may be associated with a membrane that is selectively permeable only to the analyte to which the portion is sensitive. When a plurality of analyte-sensitive portions is included, the analyte-sensitive portions, as shown in FIG. 6B may be arranged in a gauge-like pattern so as to provide a visual indication of the analyte concentration as viewed within a range of analyte concentrations, optionally to provide a gradation for the entire range.

The analyte-sensitive portion may contain one or more chemicals adapted to indicate the presence or concentration of one or more analytes though a color change. For example, addition of $CO_2$ to an aqueous bicarbonate solution will generally decrease the pH of the solution. Thus, the analyte-sensitive portion may contain an immobilized solution of water having a pH indicator to indicate the presence of $CO_2$ Chemicals are well known in the art that may serve as pH indicators and include, for example, methyl red and methyl purple. A more sophisticated version may contain, for example, a composition that contains a mixture of chemicals wherein a component of the mixture is selected to react with a particular analyte to produce a reaction product that causes another component of the mixture to change color. One of ordinary skill in the art will recognize that such compositions may be formulated for many classes of analytes, including but not limited to gaseous analytes such as oxygen, carbon dioxide, nitrous oxide, desflurane, enflurane, halothane, isoflurane, methoxyflurane, or sevoflurane.

In certain instances, the sensor may respond differently to an analyte depending on the temperature of the sensor. Thus, to ensure proper analysis of signals from the analyte-sensitive portion, the temperature of the sensor may have to be determined and taken into account. Temperature may be measured through use of a thermocouple as discussed below. The temperature of the patient may also be measured and employed in as a part of a comprehensive evaluation of the physical status of the patient.

It should also be noted that other types of sensors may be used in conjunction with the present invention. Although the sensor is used to determine the quantity of concentration of an analyte in the region of the body tissue, the measurement may or may not be direct. For example, the sensor may be constructed to measure pH or blood flow to determine the quantity or concentration of $O_2$ in the tissue since pH and/or blood flow exhibits a direct correlation to $O_2$ concentration. The same sensor may be used to determine the concentration of quantity of $CO_2$ in the issue since pH and/or blood flow exhibits a generally inverse correlation to $CO_2$ concentration. Blood flow and pH sensor are known in the art and examples of which are described in U.S. Pat. No. 6,258,046 to Kimball et al. Sensors that may be used to measure other indicators of metabolic activity, e.g., NAD(H) FAD, ADP, ATP, are known as well.

Using the Inventive Device:

In operation, the device is held in place against a tissue surface of a patient or on the epidermis, either by hand or through a holding means. The tissue may be epidermal, as noted, or nonepidermal and if nonepidermal is preferably mucosal. When a mucosal surface is involved, the probe is typically rendered immobile without using an adhesive. This is advantageous since adhesives may interfere with analyte detection by providing a chemical source that may react with the analyte. When the surface is epidermal, adhesives and gels are typically used as discussed above. When an isolation means is employed in combination with holding means, the device may provide an accurate and precise measurement of analyte concentration or quantity.

Figure 4:
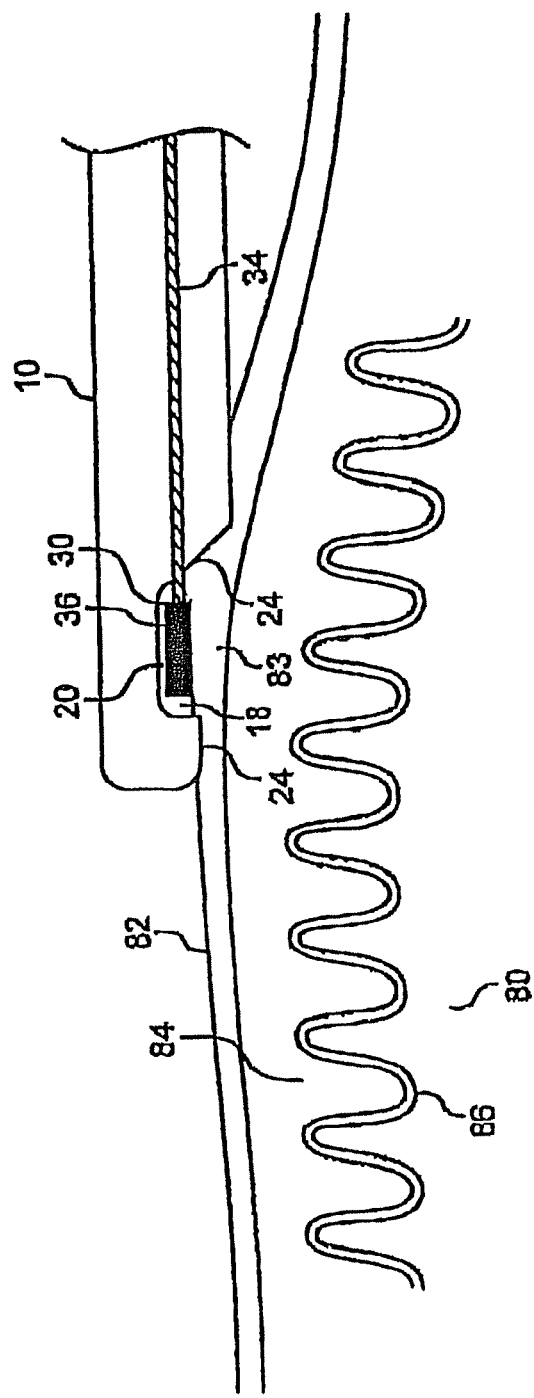
FIG. 4 illustrates the manner in which the device illustrated in FIG. 1 may be employed to detect a gaseous analyte from within a tissue.

FIG. 4 illustrates the interaction of the probe 10 with a tissue 80 to be measured for analyte concentration or quantity in a trans-tissue mode. When a tissue is to be measured non-invasively, access to a surface of the tissue must already be present. This can be accomplished through existing orifices such as the mouth, nares, ears, anus, etc., or after the tissue is exposed due to a surgical procedure. In any event, the outermost layer of the tissue surface 82 is generally exposed to ambient air. The difference between the analyte concentration of the tissue and the analyte concentration in ambient air is often large enough to render useless ordinary analyte measurement techniques taking place at the outermost layer of the tissue. That is, analyte concentration values arising from such measurement techniques do not accurately represent either the analyte concentration in ambient air or the underlying tissue 84. Therefore, some sensors such as oxygen saturation and Doppler blood flow sensors transmit electromagnetic energy into the tissue; the tissue or analyte affects the electromagnetic energy; and the electromagnetic energy is collected to assess parameters or analytes within the tissue. In addition, several invasive measurement techniques have been developed through the use of catheters in order to measure the quantity or concentration within a tissue.

The inventive device, in contrast, employs a sensor that accurately measures the concentration of an analyte in an area adjacent to the sensing site when analyte concentration is in equilibrium with the analyte concentration within the underlying layers of tissue. In one embodiment of the present invention, the non-invasive device accurately measures gas concentrations of the underlying tissue 84 even though the sensor utilized does not transmit electromagnetic energy into the tissue and is placed on the outer surface of the tissue. First, the integrated cowl 20 of probe 10 isolates the tissue from the ambient environment. As discussed above, the probe 10 is composed of a material that does not allow the ambient gases to diffuse through the cowl. The sensor 30 is optimally placed in the center of the cowl 20 to minimize the deleterious effects of probe movement, leaks through the cowl 20 and tissue, and diffusion of ambient gases through the tissue to the sensor. Once the isolating means 20 is placed on the outermost tissue surface 82, the gas concentration gradient in the tissue, caused by diffusion of ambient gases into the tissue, will dissipate. All tissue under the isolating means can equilibrate with the underlying tissue layer 84. The outermost tissue layer 82, and all tissue layers in between 83 that are under the cowl 20 will equilibrate with the underlying tissue layer 84. This equilibrium is a function of the gas concentration in the blood 86, the rate of blood flow that brings the analyte to the tissue and carries it away from the tissue, and the rate at which the tissue consumes or produces gas, thereby affecting sensor response time. The isolating means 20 of the probe has completely eliminated the ambient environment from the equation. However, one can readily observe that large movements of the probe 10 from the tissue would allow ambient air or bodily fluids onto the tissue and/or sensor and would contaminate the measurement or require that the measurement be restarted. Additionally, one can observe that occlusions due to excessive pressure on the microvascular structure can significantly affect the gas concentration measurements.

In an alternative embodiment shown in FIG. 2E, the sensor may include two optical fibers, indicated at 34 and 35. Probes including optical fibers are well suited for taking tissue measurements when the sensing site is the epidermis. Electromagnetic radiation is transmitted from a light source through the optical fiber 34 and reflected by a reflector 36. As a result, the radiation is redirected into a tissue, which may be below the surface of the skin. The radiation is allowed to interact with the analyte in the tissue before returning to the reflector and 34 into a second optical fiber 35 that is coupled to a detector.

As discussed above, the device may be used to determine the quantity or concentration of an analyte in buccal tissue by placing the device in contact with the surface of the tissue to form an enclosed region substantially enclosing the sensor. In the case of the device illustrated in FIG. 1, the cowl 20 of the probe 10 is placed within a patient's mouth and against the inner cheek to order to measure the analyte quantity or concentration in the inner cheek tissue. The contact surface 24 of the probe is contacted with the inner cheek surface so that the cowl 20 and the cheek surface enclose the analyte-sensitive portion 36 of the sensor 30. The clip 50 is contacted with the outer surface of the cheek and, in combination with the probe 10, secures the device adjacent to the surface of the inner cheek. Once in place, the concentration of the analyte in the enclosed region is allowed to reach substantial equilibrium with the concentration of analyte within the tissue. Equilibrium may be achieved by immobilizing the device with respect to the surface of tissue for a predetermined period. Then, the device may either continuously monitor the concentration of analyte in the measurement region of the tissue or measure the concentration at one or more isolated points in time. Optionally, the sensor may be exposed to analyte at a predetermined concentration in a calibrant, before using the sensor to measure an analyte to calibrate the sensor, or after using the sensor to verify that the sensor is properly calibrated.

The measured analyte concentration or sensor response may then be correlated to a condition of the patient such as perfusion failure. Alternatively or additionally, the response may be correlated to blood gas concentration, the blood gases including but not limited to oxygen, carbon dioxide, nitrous oxide, desflurane, enflurane, halothane, isoflurane, methoxyflurane, and sevoflurane, as discussed above. The inventive device may also be employed to provide an indication of parameters such as blood flow, oxygen saturation, pH, $K^+$, $Ca^{++}$, glucose, enzymes, proteins, coenzymes, $CO_2$, $pCO_2$, $O_2$, pyruvate, acetyl-CoA, citrate, isocitrate, alpha-ketoglutarate, succinyl-CoA, ADP, ATP, succinate, fumarate, malate oxaloacetate, NAD, NADH, and other analytes associated with the tricarboxylic acid cycle, collagen, elastin, melanin, and other like parameters associated with the body tissue, that if measured, can provide diagnostic value to a clinician.

Such correlation may be carried out using appropriate means, many of which are commercially available. Data acquisition circuitry described below, for example, may be used to facilitate $CO_2$ data analysis. Such circuitry includes preamplifier and amplifier, which deliver signals representing the $CO_2$ level to an analog/digital converter. The converter output is delivered to a memory that stores the values and delivers them to a central processing unit ("CPU"). Software for instructing the CPU to operate on the data is contained in memory. Pertinent information, such as characteristics of the patient, can be input through a keyboard. $CO_2$ levels are delivered to the CPU at a sufficient rate. The CPU uses these data and the elapsed time from a clock to deliver signals indicating the perfusion state of the patient.

Alternatively, the signals displayed may simply indicate the $pCO_2$ value, from which one skilled in the art can evaluate the degree of perfusion failure. When the signals represent the output of a $CO_2$ data analysis program, and thus the degree of perfusion failure, various types of indicator means can be used. For example, if the patient's condition is poor, a red light may be illuminated; if the patient's condition is stable, a green light may be illuminated; and if the patient's condition is guarded, a yellow light may be illuminated. This simplistic output is useful for moderately skilled persons such as medics in the armed forces and paramedics on ambulances. An indication of the patient's condition enables the health worker to determine whether or not the patient should be rushed to a treatment center and/or whether certain steps should be taken to enhance perfusion such as repeated depression of the chest.

The software that controls the CPU can be programmed to determine which of the three signals (red light, green light, or yellow light) should be displayed. In general, a particularly high level of carbon dioxide Z, as well as a low level of carbon dioxide Y, is established. These high and low levels may be, for example, a Z value of 80 mm Hg and a Y value of 50 mm Hg. In addition, the CPU continually determines the rate of increase or decrease of $pCO_2$. A rate of $pCO_2$ increase of more than 20 mmHg/hr indicates a high degree of perfusion failure, while, in comparison, a rate of $pCO_2$ increase less than 20 mmHg/hr connotes a lower degree of perfusion failure. If the $pCO_2$ level is decreasing, the condition of the patient is viewed as improving or stabilizing.

Similarly, software and hardware may be employed in order to indicate other parameters of diagnostic value discussed above. Further, the hardware and software may employ algorithms known in the art for optimal interpretation of signals generated from the sensors. For example, such software and hardware may be employed for component analysis. Such analysis may involve univariate regression, multivariate regression, principal component analysis or neural network processing. Techniques such as signal conditioning, signal smoothing using, e.g., smoothing, second derivative methods are known in the art and may be employed in conjunction with the invention.

Detachability/Disposability

Depending on the desired manner of use for the device, various components of the inventive device may be detachably or nondetachably coupled. For instance, certain components of the device may be designed for single-use while other components may be reusable. However, such components must function as a whole during any particular use. Thus, certain components must be in an operative coupled relationship that may involve, for example, immobilization of the components with respect to each other. Such coupling may involve, for example, providing mating surfaces, fastening means, locking mechanisms, or other means known to one of ordinary skill in the art for detachable or nondetachable coupling.

To provide an example of how the inventive device may incorporate detachability in its construction, FIG. 6 illustrates that the sensor 30 is slid or inserted into a cavity 19 of the probe 10. Thus, the sensor may be provided a detachable component from the probe. In addition, other detachable components may be provided as well. As discussed above, depending on the construction of the probe and/or the sensor, the devices as described herein may be adapted for single (disposable) or multiple use. When a multiple-use probe is placed within a patient's body, such as in the mouth or the nares, the probe may come into contact with saliva or other body fluids that may transmit pathogens from one patient to another. This is particularly problematic when analyte detection is desired for tissue that may be susceptible to tearing, such as that of the stomach, colon, rectum, or jejunum. One way to eliminate such pathogens is through sterilization. However, sterilization may require excessive time during which the device becomes unavailable for use. Thus, a disposable sheath may be placed over the probe to reduced the risk of pathogen transmission from one patient to another through multiple or consecutive device use. In the alternative, the sheath may be reusable but may be constructed such that it is more easily sterilized than the probe.

Figure 7A:
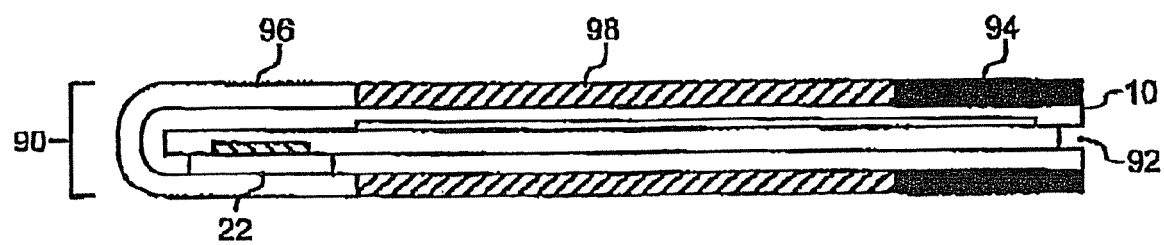
FIGS. 7A and 7B, collectively referred to as FIG. 7, illustrate disposable sheaths having an opening in a rigid proximal end through which a probe of the device may be inserted and a distal end composed of an analyte-permeable membrane that allows transmission of analyte therethrough.

As illustrated in FIG. 7A, such a disposable sheath 90 may be used to cover the device illustrated in FIG. 6A. The sheath 90 has a shape that generally conforms to the profile of the probe 10. The sheath 90 has an opening 92 at one end through which the probe can be inserted. Preferably, the portion 94 of the sheath that forms the sheath opening 92 is composed of a rigid material that forms a seal around the probe 10 when the probe is inserted into the sheath 90. The seal serves to ensure that pathogens do not contaminate the covered portion of the probe. The rigidity of the rigid portion 94 of the sheath allows the sheath to be readily removed or ejected from the probe by a mechanical ejection means (not shown) similar to those used in conventional pipetting devices. The distal tip portion 96 of the sheath 90 is adapted to fit over the distal tip of the probe 10 and is composed of an analyte-permeable material that allows transmission of the analyte therethrough. As shown, the permeable portion comprises a gas-permeable polymeric membrane. It is evident that the membrane material is selected for both analyte transmission properties and for pathogen barrier properties. In addition, it is desirable that the membrane be sufficiently thin or analyte-permeable so as to ensure sufficiently fast gas analyte transmission for quick sensor response. Suitable membrane materials include, but are not limited to, silicone-based polymers as well as perfluorinated polymers. Silicone polymers are generally permeable to $O_2$ and $CO_2$ but do not allow liquid water that may carry pathogens to be transmitted therethrough. Other common polymers that exhibit permeability to analytes but are substantially impermeable to water include, but are not limited to, poly (vinylidene chloride), latex rubber, and low density polyethylene.

Figure 7B:
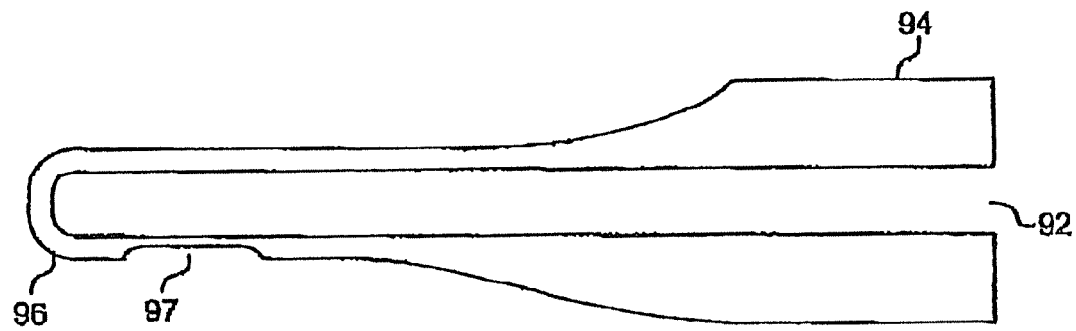

A sheath for covering the probe of the invention may be made as a single piece or by assembling a plurality of pieces. The sheath shown in FIG. 7A is constructed in three pieces. The rigid ring portion 94 is attached to tubular portion 98 that has sufficient rigidity to support its own weight but sufficient flexibility to conform to the shape of an inserted probe. Distal tip portion 96 is attached to portion 98 and, as described above, is a thin, analyte-permeable membrane. In the alternative, the sheath may be of a single piece construction as illustrated in FIG. 7B. The entire sheath of FIG. 7B is composed of a single material. The interior profile of the single-piece sheath 90 is also in the shape of the profile of the device for which the sheath is to cover. The sheath has an opening 92 at one end, i.e., the proximal end 94, through which the probe can be inserted. The wall thickness is greatest at the proximal end 94 of the sheath 90 to provide rigidity to sheath opening 92. The distal tip portion 96 of the sheath 90 is thin to ensure a sufficient analyte permeation rate for effective analyte detection by the sensor. Optionally, a particularly thin portion 97 may be provided in the sheath such that the thin portion covers the sensing area 18 of the device when the device is inserted in to the sheath. Irrespective of whether a single-piece or multiple-piece sheath is used, when a sheath-covered probe is exposed to analyte, the analyte permeable tip allows analyte communication between analyte and sensing area 18. In addition, the sheath may be constructed so as to avoid causing tissue blanching during its use. It should be noted that the sheath may be constructed so as to be placed over only a portion of the probe, e.g., to protect the sensor from contamination.

The sheath can also serve as a means for reducing interference. As discussed above, the sheath may be constructed from a material that is selectively permeable to analytes. By forming the sheath using a material that is substantially impermeable to an interfering moiety, the sheath can prevent the interfering moieties from reaching the sensor. For example, if a bodily fluid component is known to impair the performance of a sensor sensitive to a particular analyte, a sheath can serve as a means for reducing interference if the sheath allows the analyte to be transmitted therethrough while blocking the interfering component from reaching the sensor.

Figure 8:
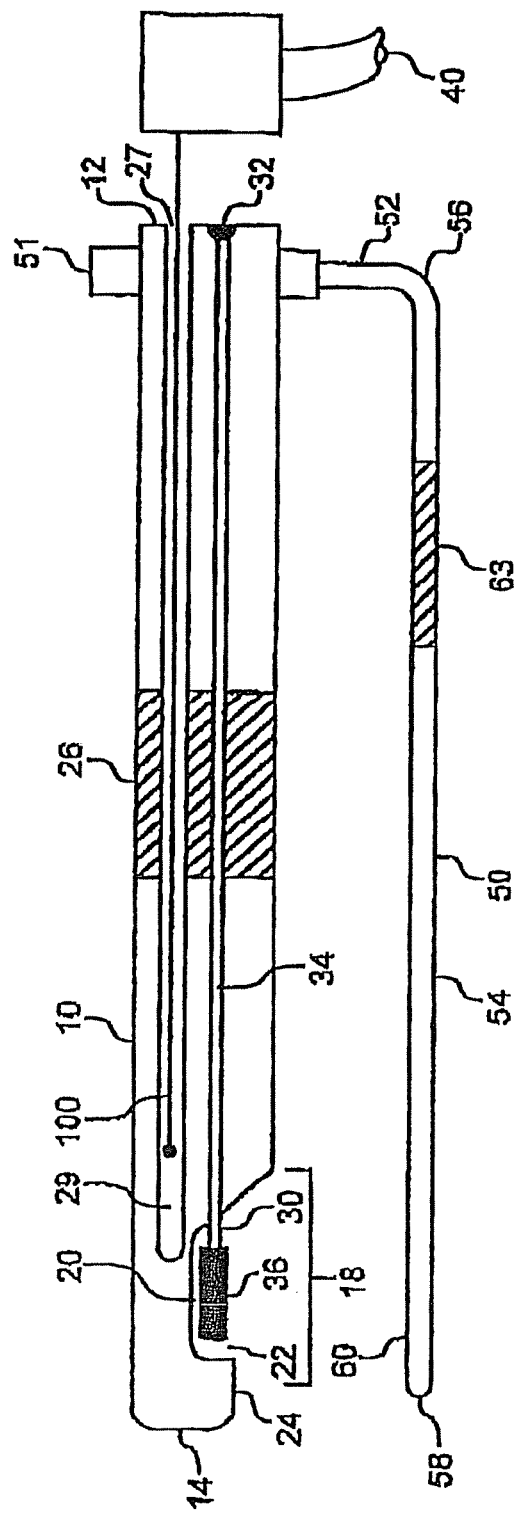
FIG. 8 illustrates in cross-sectional view another version of the device of the present invention wherein the device is operatively attachable to an indicating means having a temperature-sensing means in the faun of a thermocouple for detecting temperature at the sensor of the probe.

FIG. 8 shows another version of the device of the invention adapted for attachment to an indicating means 40 having a temperature sensing means in the form of a thermocouple 100 for detecting temperature at the sensor of the probe 10, though other forms of temperature sensing means such as a thermometer, resistive thermal device, or other thermal sensors may be employed as well. Overall, this device is similar to the device shown in FIG. 1, except that a lengthwise bore 29 is provided to extend from an opening 27 sized to receive a thermocouple, the opening located in the proximal end, extending through the probe, and terminating near sensing area 18 of cowl 20. As shown, the bore is axially offset, but the probe may be designed such that the bore extends along the probe's axis as long as an inserted thermocouple can detect the temperature at or near the sensor. As discussed above, an indicating means 40 having a temperature sensing means extends therefrom in the form of a thermocouple 100. The indicating means is constructed to allow the thermocouple to be inserted into the opening of the probe and allow for operative connection with the connector of the sensor. Once connected, the indicating means through a gauge indicates the concentration of the analyte that is adjusted for temperature as measured by the thermocouple. The indicating means may also be adapted to indicate a condition of the patient such as perfusion failure or the degree to which a patient has been anaesthetized. In any case, this probe construction is particularly suitable for disposable probes since an incorporated thermocouple necessarily adds cost to the device.

In the alternative, the temperature sensing means, i.e., the thermocouple, can be constructed such that it is permanently affixed to the probe to measure the temperature of the sensor or the patient. In such a case, the indicating means is constructed to allow connection with both the sensor connector and the thermocouple.

Thus, it should be evident that the inventive device may involve varying degrees of disposability. For example, the inventive device may employ a reusable sensor to measure the partial pressure of $O_2$, delivered $O_2$, partial pressure of $CO_2$, pH, blood flow, or other physiological parameters but employ a disposable probe. Alternatively the inventive device may employ a reusable probe in combination with a disposable sensor. Other combinations may be discovered through routine experimentation upon practice of the invention.

Variations of the present invention will be apparent to those of ordinary skill in the art. Further, it is to be understood that while the invention has been described in conjunction with the preferred specific embodiments thereof, that the foregoing description is intended to illustrate and not limit the scope of the invention. Other aspects, advantages, and modifications within the scope of the invention will be apparent to those skilled in the art to which the invention pertains.

All patents, patent documents, and other references cited herein are hereby incorporated by reference in their entireties.

The invention claimed is:

1. A device for contacting a tissue sensing site of a patient to determine a physiologic parameter of the patient, comprising:
    a probe body having a longitudinal axis, a top covered portion parallel to said longitudinal axis, said top portion comprising a material that is impermeable and a bottom open portion defining a perimeter structured to be positioned against a surface of the tissue sensing site, said perimeter defining a recess therewithin, said probe body and said perimeter structured to prevent application of excessive pressure to the sensing site to allow for substantially undisturbed blood flow in the tissue; and
    a sensor responsive to a concentration of an analyte through a chemical reaction with a reactant, said analyte concentration representative of the physiologic parameter, said sensor having a first end and a sensor body, said first end coupled to said probe body and said sensor body unobstructedly suspended with the recess;
    wherein upon placement of the probe body against the sensing site, said impermeable top portion and said perimeter are structured to create a covered, isolated measurement area within the recess such that the sensor is exposed to the tissue sensing site and the covered, isolated measurement area prevents the analyte from dissipating from the measurement area.

2. The device of claim 1, wherein the probe body further comprises a means for reducing interference at the sensing site.

3. The device of claim 2, wherein the means for reducing interference at the sensing site is an integral portion of the probe.

4. The device of claim 1, wherein the probe is constructed to allow the sensor to be secured at the sensing site.

5. The device of claim 4, wherein a surface of the probe is secured to the sensing site with an adhesive.

6. The device of claim 1, wherein the sensor is detachable from the probe body.

7. The device of claim 2, wherein the means for reducing interference is adapted to reduce interference from electromagnetic radiation, air flow or both.

8. The device of claim 3, wherein the means for reducing interference comprises an isolating means for isolating and preventing said analyte from dissipating from the measurement area and for allowing the analyte to come into equilibrium within the measurement area.

9. The device of claim 8, wherein the isolating means for isolating and preventing an analyte from dissipating from the measurement area represents an integral portion of the probe.

10. The device of claim 1, wherein the device is sized to fit into the nares, mouth, or cheek of the patient.

11. The device of claim 1 wherein the analyte is selected from the group consisting of hydrogen ions, $CO_2$, $pCO_2$, $O_2$, glucose, pyruvate, acetyl-CoA, citrate, isocitrate, alpha-ketoglutarate, succinyl-CoA, ADP, ATP, succinate, fumarate, malate oxaloacetate, NAD, NADH, and combinations thereof.

12. The device of claim 1, further comprising an indicating means for indicating analyte concentration in the patient, said indicating means operably connected to the sensor.

13. The device of claim 1, wherein at least a portion of the probe body comprises a material that allows the portion to deform in response to force applied to the probe body so as to avoid substantial blanching the tissue.

14. The device of claim 13, wherein the material is an elastically deformable polymer selected from the group consisting of polyethylene, polypropylene, polybutylene, polyamide, polyimide, polyester, perfluorinated polymer, polystyrene, polyvinyl chloride and elastomers.

15. The device of claim 1, wherein the device includes a holding means for securing the probe body to the sensing site.

16. The device of claim 15, wherein the holding means is selected from the group consisting of a clip, handle, clamp, adhesives, gels, fasteners, strap, belt, hook, sutures, and staples.

17. The device of claim 15, wherein the holding means is adapted to secure the probe body to the sensing site without applying a pressure greater than about $1.5 \times 10^4$ pascals to the tissue.

18. The device of claim 1, wherein the analyte to which the sensor is responsive is a gas selected from the group consisting of oxygen, carbon dioxide, nitrous oxide, desflurane, enfluran, halothane, isoflurane, methoxyflurane, and sevoflurane.

19. The device of claim 1, further comprising at least one additional sensor.

20. The device of claim 1, wherein the device further comprises a temperature detecting means for detecting temperature at the sensor.

21. The device of claim 20, wherein the temperature detecting means is detachable from the device.

22. The device of claim 1, further comprising a sheath covering the device.

23. The device of claim 22, wherein the device is adapted for single use.

24. The device of claim 22, wherein the sheath has a selectively permeable portion that allows transmission of an analyte therethrough.

25. The device of claim 24, wherein the selectively permeable portion is selected from the group consisting of a silicone, a porous membrane and combinations thereof.

26. The device of claim 22, wherein the sheath includes a rigid portion.

27. The device of claim 22, wherein the sheath is disposable.

28. The device of claim 19, wherein the device is adapted to be reused.

29. The device of claim 1, wherein the sensing site is nonepidermal tissue.

30. The device of claim 29, wherein the tissue is mucosal.

31. The device of claim 1, wherein the sensing site is the patient's epidermis.

32. The device of claim 1, wherein the sensor is a Severinghaus-type sensor.

33. The device of claim 1, wherein the sensor is responsive to analyte concentration through generation or alteration of an electrical current.

34. A method for determining a physiologic parameter of a patient, the method comprising:
    (a) providing the probe of claim;
    (b) placing the probe body on the sensing site without substantially disturbing blood flow within the tissue such that the impermeable top portion and the perimeter of the bottom portion define an isolated, covered measurement region that prevents analyte from dissipating from the measurement region; and
    (c) providing a computing device programmed to derive the physiologic parameter from the response of the sensor to the concentration of the analyte present in the measurement region.

35. The method of claim 34, further comprising, exposing the sensor to at least one analyte at a predetermined concentration in at least one calibrant.

36. The method of claim 34, wherein the analyte is selected from the group consisting of hydrogen ions, $CO_2$, $pCO_2$, $O_2$, glucose, pyruvate, acetyl-CoA, citrate, isocitrate, alphaketoglutarate, succinyl-CoA, ADP, ATP, succinate, fumarate, malate oxaloacetate, NAD, NADH, and combinations thereof.

37. The method of claim 1, wherein the sensing site is mucosal tissue.

38. The method of claim 34, further comprising allowing the concentration of the analyte in the measurement region to reach an equilibrium level.

39. The method of claim 34, further comprising immobilizing the probe on the sensing site for a predetermined period.

40. The method of claim 39, wherein deriving an assessment of the concentration of the analyte in the measurement site is initiated, repeated or performed continuously during the predetermined period of time.

41. The method of claim 34, further comprising processing sensor output to a condition of the patient.

42. The method of claim 41, wherein the condition is a regional condition, a systemic condition, perfusion failure, tissue gas concentration, tissue pH or tissue activity.

43. The method of claim 41, said processing is carried out using a predictive algorithm, endpoint detection and/or verification, and/or univariate, multivariate, or neural network analysis.

* * * * *